(12) United States Patent
Hoyme et al.

(10) Patent No.: US 9,145,346 B1
(45) Date of Patent: Sep. 29, 2015

(54) PROCESS FOR 2,2,4,4-TETRAMETHYLCYCLOBUTANE-1,3-DIOL CRYSTALLIZATION

(71) Applicant: Eastman Chemical Company, Kingsport, TN (US)

(72) Inventors: Craig Alan Hoyme, Kingsport, TN (US); Shane Kipley Kirk, Church Hill, TN (US)

(73) Assignee: Eastman Chemical Company, Kingsport, TN (US)

( * ) Notice: Subject to any disclaimer, the term of this patent is extended or adjusted under 35 U.S.C. 154(b) by 0 days.

(21) Appl. No.: 14/566,091

(22) Filed: Dec. 10, 2014

(51) Int. Cl.
*C07C 29/78* (2006.01)

(52) U.S. Cl.
CPC ............. *C07C 29/78* (2013.01); *C07C 2101/04* (2013.01)

(58) Field of Classification Search
CPC ..................................................... C07C 29/78
See application file for complete search history.

(56) References Cited

U.S. PATENT DOCUMENTS

| | | |
|---|---|---|
| 1,602,699 A | 10/1926 | Nightingale |
| 2,160,841 A | 6/1939 | Dreyfus |
| 2,202,046 A | 5/1940 | Dreyfus et al. |
| 2,278,537 A | 4/1942 | Dreyfus et al. |
| 2,806,064 A | 9/1957 | Mcklveen |
| 2,901,466 A | 8/1959 | Kibler |
| 2,936,324 A | 5/1960 | Hasek et al. |
| 3,000,906 A | 9/1960 | Hasek et al. |
| 3,030,335 A | 4/1962 | Goldberg |
| 3,190,928 A | 6/1965 | Elam et al. |
| 3,201,474 A | 8/1965 | Hasek et al. |
| 3,227,764 A | 1/1966 | Martinet et al. |
| 3,236,899 A | 2/1966 | Clark et al. |
| 3,259,469 A | 7/1966 | Painter et al. |
| 3,287,390 A | 11/1966 | Poos et al. |
| 3,288,854 A | 11/1966 | Martinet et al. |
| 3,312,741 A | 4/1967 | Martinet et al. |
| 3,329,722 A | 7/1967 | Rylander |
| 3,366,689 A | 1/1968 | Maeda et al. |
| 3,403,181 A | 9/1968 | Painter |
| 5,118,847 A | 6/1992 | Jackson et al. |
| 5,169,994 A | 12/1992 | Sumner et al. |
| 5,258,556 A | 11/1993 | Sumner et al. |
| 5,475,144 A | 12/1995 | Watson et al. |
| 6,232,504 B1 | 5/2001 | Barteau et al. |
| 6,600,080 B1 | 7/2003 | Nagamura et al. |
| 6,919,489 B1 | 7/2005 | McCusker-Orth |
| 7,335,800 B2 | 2/2008 | Komplin et al. |
| 7,521,583 B2 | 4/2009 | McCusker-Orth et al. |
| 7,524,994 B2 | 4/2009 | McCusker-Orth et al. |
| 7,560,600 B2 | 7/2009 | McCusker-Orth et al. |
| 7,582,804 B2 | 9/2009 | McCusker-Orth et al. |
| 7,723,551 B2 | 5/2010 | McCusker-Orth et al. |
| 7,838,707 B2 | 11/2010 | McCusker-Orth et al. |
| 7,989,667 B2 | 8/2011 | O'Meadhra |
| 8,394,997 B2 | 3/2013 | Liu et al. |
| 8,420,868 B2 | 4/2013 | Liu et al. |

OTHER PUBLICATIONS

Hasek, et al. Chemistry of Dimethylketone Dimer. Journal of Organic Chemistry, 1961, vol. 26, pp. 700-704.

Sprague et al., Hydrogentation and Hydrogenolysis of 1,3-Diketones. Journal of the American Chemical Society, 1934, vol. 56, pp. 2669-2675.

*Primary Examiner* — Brian J Davis
(74) *Attorney, Agent, or Firm* — Tammys L. Taylor

(57) ABSTRACT

A process for isolating 2,2,4,4-tetramethyl-1,3-cyclobutane-diol (TMCD) by (a) crystallizing TMCD in a crystallization zone to generate a slurry comprising TMCD solids and (b) isolating the TMCD solids in a solid liquid separation zone to generate a wet cake and a mother liquor stream.

30 Claims, 7 Drawing Sheets

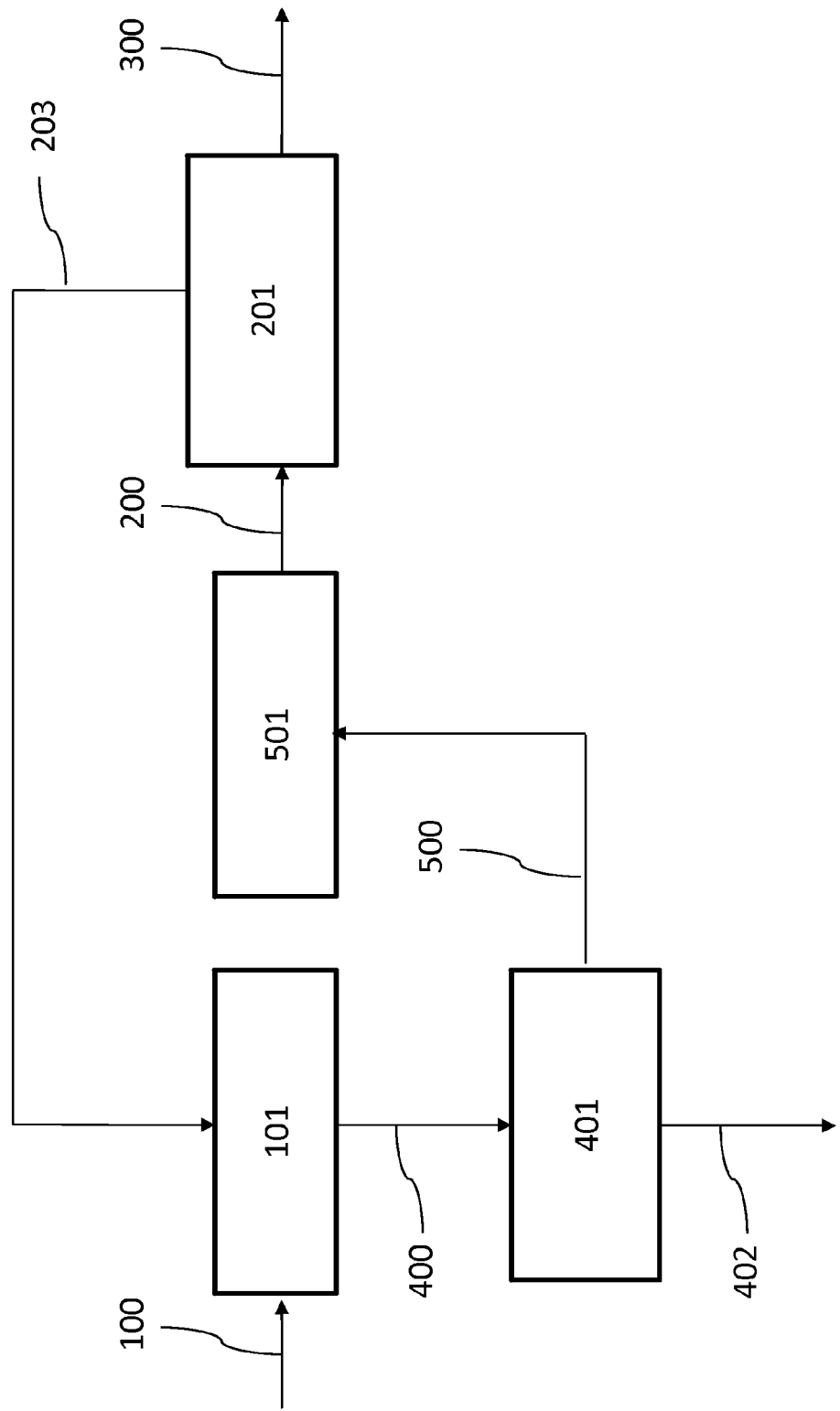

US 9,145,346 B1

PROCESS FOR 2,2,4-TETRAMETHYLCYCLOBUTANE-1,3-DIOL CRYSTALLIZATION

FIELD OF THE INVENTION

The present disclosure generally relates to a novel process for the crystallization of a mixture of cis-2,2,4,4-tetramethylcyclobutane-1,3-diol and trans-2,2,4,4-tetramethylcyclobutane-1,3-diol dissolved in a solvent. The present disclosure generally further relates to the crystallization processes that yield solid cis-2,2,4,4-tetramethylcyclobutane-1,3-diol and solid trans-2,2,4,4-tetramethylcyclobutane-1,3-diol with improved filterability.

BACKGROUND OF THE INVENTION

U.S. Pat. Nos. 5,258,556 and 5,169,994 describe the isolation of the product from the hydrogenation step (2,2,4,4-tetramethylcyclobutanediol) by either a distillation or crystallization technique. In the examples in these patents, the isolation method by crystallization is described as cooling the filtered, post-hydrogenation mixture to room temperature and separating the product from the solvent.

However, this crystallization method fails to produce a solid product from the post-hydrogenation mixture that can meet a number of stringent criteria necessary for the product to perform satisfactorily in downstream processes. These criteria generally relate to the yield of product, the shape of the crystal size distribution, the ease of isolation of the formed crystallization solids, the amount of adhering moisture remaining on the crystal surfaces after filtration, and the moisture content of the filtered product.

In general, the yield of product from a single pass crystallization operation should be maximized. A low yield of dissolved material is both materially and economically inefficient.

Ideally, the shape of the crystal size distribution generated in the crystallization zone should be such that the quantity of "fines" is minimized. "Fines" are particles that tend to plug the pores of the filter or that fill the gaps between larger particles on a filter, which results in reduced flow rate of liquid through the filter. "Fines" particles are known to require long filtration times and to produce dust when dried that provides a safety hazard.

Isolation of the formed crystallization solids is usually performed using a mechanical filtration device, such as a filter or centrifuge. The shape of the crystal size distribution should also be such that the driving force for filtration is minimized and the surface area required for the filtration is also minimized. This would yield a smaller filtration device that can operate at faster filtration rates.

Typically, the amount of adhering moisture remaining on the crystal surfaces after filtration should also be minimized. High surface moisture content increases the probability of impurity entrainment to successive operations.

In general, the moisture content of the filtered product should be low enough so that the successive drying operation has minimum energy demands and requires a short processing time.

U.S. Pat. Nos. 5,258,556 and 5,169,994 describe a batch process to crystallize 2,2,4,4-tetramethylcyclobutanediol from solution. However, for a large scale process, it is more economical to use a continuous process to isolate the product from solution as this eliminates the need for complex heat transfer equipment, seeding protocols and additional storage equipment typically used for batch operations. Continuous processes are also easier to control due to a small dynamic range of operation as compared to batch processing.

U.S. Pat. No. 7,989,667 discloses continuous crystallization of cis- and trans-2,2,4,4-tetramethyl-1,3-cyclobutanediol (TMCD) from isobutyl isobutyrate.

In the production of 2,2,4,4-tetramethyl-1,3-cyclobutanediol (TMCD)(CAS No. 3010-96-6), various co-products, solvents, and unconverted reactants accompany the TMCD product. The removal of these impurities from the TMCD product is advantageous for the production of TMCD as well as providing the capability to produce a high purity TMCD product. It is also desirable to have a choice of different solvents to select from in order to provide options for the isolation and purification of TMCD via crystallization. Proper solvent selection for the production of TMCD is important in removing the impurities and providing the capability to generate and recover a high purity TMCD product.

There is a need for processes that provide for the removal of the impurities and recovery of TMCD solids from a variety of solvents and solvent classes. Accordingly, the present invention is directed to addressing one or more of the needs described above.

BRIEF SUMMARY OF THE INVENTION

The present disclosure is directed to novel processes for the crystallization from a mixture of cis-2,2,4,4-tetramethylcyclobutanediol and trans-2,2,4,4-tetramethylcyclobutanediol dissolved in a solvent. The crystallization processes of the invention have improved isolated product yield and purity.

In one aspect, the invention relates to a process for the crystallization from a mixture comprising cis-2,2,4,4-tetramethylcyclobutanediol and trans-2,2,4,4-tetramethylcyclobutanediol dissolved in a solvent, the process comprising:
  (a) crystallizing at least a portion of 2,2,4,4-tetramethylcyclobutanediol in a crystallization zone operated at a temperature such that the concentration of 2,2,4,4-tetramethylcyclobutanediol in the crystallization zone is above the saturated concentration of 2,2,4,4-tetramethylcyclobutanediol to form a slurry comprising 2,2,4,4-tetramethylcyclobutanediol and the solvent;
  (b) transferring the slurry from the crystallization zone to a solid-liquid separation zone,
  (c) separating the slurry into a mother liquor stream comprising the solvent and dissolved 2,2,4,4-tetramethylcyclobutanediol and into a wet cake stream comprising at least a portion of the crystallized 2,2,4,4-tetramethylcyclobutanediol,
  wherein the solvent comprises an alkyl acetate, an alkyl propionate, an alkyl carbonate, an alkyl alcohol, an aromatic hydrocarbon, an alkyl ketone, an alkyl glycol, a blend of (1) an alkyl hydrocarbon and (2) an alkyl ester, or water or mixtures thereof.

In another aspect, the invention relates to a process for the crystallization from a mixture comprising cis-2,2,4,4-tetramethylcyclobutanediol and trans-2,2,4,4-tetramethylcyclobutanediol dissolved in a solvent, the process comprising:
  (a) crystallizing at least a portion of one of the 2,2,4,4-tetramethylcyclobutanediol isomers in the crystallization zone which is operated at a temperature such that the concentration of the crystallized 2,2,4,4-tetramethylcyclobutanediol isomer is above its saturated concentration and the other isomer concentration is below its saturated concentration to form a slurry of the crystallized isomer,
  (b) transferring the slurry to the solid-liquid separation zone, wherein at least a portion of the slurry is separated into a mother liquor stream comprising the solvent and dissolved 2,2,4,4-tetramethylcyclobutanediol and into a wet cake stream comprising at least a portion of the crystallized isomer of 2,2,4,4-tetramethylcyclobutanediol, wherein the crystallized isomer of 2,2,4,4-tetramethylcyclobutanediol comprises at least 90 weight % of one isomer, based on the total weight of the crystallized 2,2,4,4-tetramethylcyclobutanediol, and wherein the solvent comprises an alkyl acetate, an alkyl propionate, an alkyl carbonate, an alkyl alcohol, an aromatic hydrocarbon, an alkyl ketone, an alkyl glycol, a blend of (1) an alkyl hydrocarbon and (2) an alkyl ester, or water or mixtures thereof.

In another aspect, the invention relates to a process for the crystallization from a mixture comprising cis-2,2,4,4-tetramethylcyclobutanediol and trans-2,2,4,4-tetramethylcyclobutanediol dissolved in a solvent, the process comprising:
  (a) crystallizing at least a portion of 2,2,4,4-tetramethylcyclobutanediol in a first crystallization zone operated at a temperature such that the concentration of 2,2,4,4-tetramethylcyclobutanediol in the first crystallization zone is above the saturated concentration of 2,2,4,4-tetramethylcyclobutanediol to form a first slurry comprising crystallized 2,2,4,4-tetramethylcyclobutanediol and the solvent,
  (b) transferring at least a portion of the first slurry to a second crystallization zone independently from the transfer of at least a portion of a first mother liquor from the first crystallization zone to the second crystallization zone,
  (c) crystallizing at least a second portion of 2,2,4,4-tetramethylcyclobutanediol in the second crystallization zone operated at a temperature such that the concentration of 2,2,4,4-tetramethylcyclobutanediol in the second crystallization zone is above the saturated concentration of 2,2,4,4-tetramethylcyclobutanediol to form a second slurry comprising the second portion of 2,2,4,4-tetramethylcyclobutanediol and the solvent,
  (d) transferring the second slurry to a solid-liquid separation zone,
  (e) separating the second slurry into a second portion of mother liquor stream comprising the solvent and the dissolved 2,2,4,4-tetramethylcyclobutanediol and into a wet cake stream comprising the second portion of crystallized 2,2,4,4-tetramethylcyclobutanediol;
wherein the solvent comprises an alkyl acetate, an alkyl propionate, an alkyl carbonate, an alkyl alcohol, an aromatic hydrocarbon, an alkyl ketone, an alkyl glycol, a blend of (1) alkyl hydrocarbons and (2) alkyl esters, or water or mixtures thereof.

In another aspect, the invention relates to a process for the crystallization from a mixture comprising cis-2,2,4,4-tetramethylcyclobutanediol and trans-2,2,4,4-tetramethylcyclobutanediol dissolved in a solvent, the process comprising:
  (a) crystallizing at least a portion of one of the 2,2,4,4-tetramethylcyclobutanediol isomers in the first crystallization zone which is operated at a temperature such that the feed concentration of one of the isomers is above its saturated concentration and the other feed isomer concentration is below its saturated concentration to form a first slurry comprising at least 90 weight % of one crystallized isomer, based on the total weight of the crystallized isomers,
  (b) transferring the first slurry from the first crystallization zone to the second crystallization zone independently from the transfer of at least a portion of a first mother liquor from the first crystallization zone to the second crystallization zone,
  (c) crystallizing at least a second portion of one of the 2,2,4,4-tetramethylcyclobutanediol isomers in a second crystallization zone which is operated at a temperature such that the concentration of one of the isomers is above its saturated concentration and the other isomer is below its saturated concentration to form a second slurry comprising at least 90 weight % of a the crystallized isomer, based on the total weight of the crystallized isomers;
  (d) transferring the second slurry to a solid-liquid separation zone, wherein the second slurry is separated into a second mother liquor stream comprising the solvent and the dissolved 2,2,4,4-tetramethylcyclobutanediol and into a wet cake stream comprising at least 90 weight % of the crystallized isomer, based on the total weight of the crystallized isomers, of 2,2,4,4-tetramethylcyclobutanediol,
wherein the solvent comprises an alkyl acetate, an alkyl propionate, an alkyl carbonate, an alkyl alcohol, an aromatic hydrocarbon, an alkyl ketone, an alkyl glycol, a blend of (1) an alkyl hydrocarbon and (2) an alkyl ester, or water or mixtures thereof.

In another aspect, the invention relates to a process for the crystallization from a mixture comprising cis-2,2,4,4-tetramethylcyclobutanediol and trans-2,2,4,4-tetramethylcyclobutanediol dissolved in a solvent, the process comprising:
  (a) crystallizing at least a portion of one of the 2,2,4,4-tetramethylcyclobutanediol isomers in the first crystallization zone which is operated at a temperature such that the feed concentration of one of the isomers is above its saturated concentration and the other isomer feed concentration is below its saturated concentration to form a first slurry of comprising at least 90 weight % of one crystallized isomer, based on the total weight of crystallized isomers,
  (b) transferring the first slurry to a solid liquid separation zone wherein the first slurry is separated into a first mother liquor stream comprising the solvent and the dissolved 2,2,4,4-tetramethylcyclobutanediol and into a first wet cake stream comprising at least a portion of the crystallized isomer of 2,2,4,4-tetramethylcyclobutanediol
  (c) transferring the first mother liquor stream to a second crystallization zone wherein both 2,2,4,4-tetramethylcyclobutanediol isomers are crystallized to form a second slurry comprising cis- and trans-2,2,4,4-tetramethylcyclobutanediol and the solvent;
  (d) transferring the second slurry to a second solid liquid separation zone,
  (e) separating the second slurry into a second mother liquor stream comprising the solvent and the dissolved 2,2,4,4-tetramethylcyclobutanediol and into a second wet cake stream comprising the crystallized cis- and trans-2,2,4,4-tetramethylcyclobutanediol; wherein the solvent comprises an alkyl acetate, an alkyl propionate, an alkyl carbonate, an alkyl alcohol, an aromatic hydrocarbon, an alkyl ketone, an alkyl glycol, a blend of (1) an alkyl hydrocarbon and (2) an alkyl ester, or water or mixtures thereof.

In another aspect, the invention relates to a process for the crystallization of a mixture comprising cis-2,2,4,4-tetramethylcyclobutanediol and trans-2,2,4,4-tetramethylcyclobutanediol dissolved in a solvent, the process comprising:
  (a) crystallizing at least a portion of 2,2,4,4-tetramethylcyclobutanediol in a crystallization zone operated at a temperature such that the concentration of 2,2,4,4-tetramethylcyclobutanediol in the crystallization zone is above the saturated concentration of 2,2,4,4-tetramethylcyclobutanediol to form a slurry comprising crystallized 2,2,4,4-tetramethylcyclobutanediol and the solvent;
(b) transferring the first slurry to a solid liquid separation zone wherein the first slurry is separated into a first mother liquor stream comprising the solvent and the dissolved 2,2,4,4-tetramethylcyclobutanediol and into a first wet cake stream comprising at least a portion of the crystallized 2,2,4,4-tetramethylcyclobutanediol;
(c) transferring the first mother liquor stream to a second crystallization zone wherein 2,2,4,4-tetramethylcyclobutanediol is crystallized to form a second slurry comprising 2,2,4,4-tetramethylcyclobutanediol and the solvent;
(d) transferring the second slurry to a second solid liquid separation zone,
(e) separating the second slurry into a second mother liquor stream comprising the solvent and the dissolved 2,2,4,4-tetramethylcyclobutanediol and into a second wet cake stream comprising the crystallized 2,2,4,4-tetramethylcyclobutanediol;
(f) transferring all of the second wet cake comprising solid cis-2,2,4,4-tetramethylcyclobutanediol and solid trans-2,2,4,4-tetramethylcyclobutanediol from the second solid liquid separation zone to the first crystallization zone, wherein the solvent comprises an alkyl acetate, an alkyl propionate, an alkyl carbonate, an alkyl alcohol, an aromatic hydrocarbon, an alkyl ketone, an alkyl glycol, a blend of (1) an alkyl hydrocarbon and (2) an alkyl ester, or water or mixtures thereof.

In another aspect, the invention relates to a process for the crystallization from a solvent excluding isobutyl isobutyrate.

In another aspect, all embodiments of the invention related to a process that may be run as a batch, semi-continuous or continuous process.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

BRIEF DESCRIPTION OF THE DRAWINGS

FIG. 7 is a block flow diagram of a single-zone crystallization process to isolate mixed isomers of TMCD and with mother liquor recycle to a second single-zone crystallization process to isolate a mixture of cis- and trans-2,2,4,4-tetramethylcyclobutane-1,3-diol and with recycle of all of the TMCD solids to the first single-zone crystallization zone.

DETAILED DESCRIPTION

Figure 1:
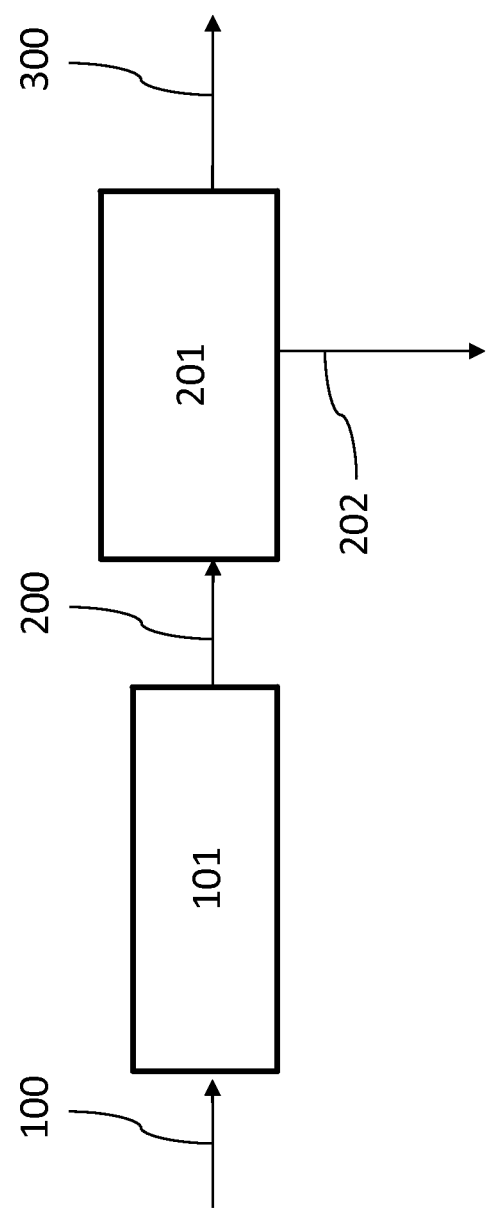
FIG. 1 is a block flow diagram of a single-zone crystallization process with a single product isolation of cis- and trans-2,2,4,4-tetramethylcyclobutane-1,3-diol.

The present disclosure may be understood more readily by reference to the following detailed description of certain embodiments of the invention and the working examples.

In accordance with the purposes of this invention, certain embodiments of the invention are described in the Summary of the Invention and are further described herein below. Also, other embodiments of the invention are described herein.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, each numerical parameter should at least be construed in light of the number of reported significant digits and by applying ordinary rounding techniques. Further, the ranges stated in this disclosure and the claims are intended to include the entire range specifically and not just the endpoint(s). For example, a range stated to be 0 to 10 is intended to disclose all whole numbers between 0 and 10 such as, for example, 1,2, 3,4, etc., as well as the endpoints 0 and 10. Also, a range associated with chemical substituent groups such as, for example, "$C_1$ to $C_5$ hydrocarbons," is intended to specifically include and disclose $C_1$ and $C_5$ hydrocarbons as well as $C_2$, $C_3$, and $C_4$ hydrocarbons.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

As used in the specification and the appended claims, the singular forms "a," "an," and "the" include their plural referents unless the context clearly dictates otherwise. For example, reference to the processing or crystallizing in a "zone," is intended to include the processing or crystallizing in more than one zone. References to a composition containing or including "a" given component or product is intended to include other components or products, in addition to the one named.

By "comprising" or "containing" or "including" we mean that at least the named compound, element, particle, or method step, etc., is present in the composition or article or method, but we do not exclude the presence of other compounds, catalysts, materials, particles, method steps, etc., even if the other such compounds, materials, particles, method steps, etc., have the same function as what is named, unless expressly excluded in the claims.

The terms "TMCD", "2,2,4,4-tetramethylcyclobutane-1, 3-diol", "2,2,4,4-tetramethylcyclobutanediol," "2,2,4,4-tetramethyl-1,3-cyclobutanediol" are used interchangeably and include the cis and trans isomers unless indicated otherwise. The term "saturated concentration," as used herein, means the concentration at which no more solid isomer can be dissolved in solution at a given temperature.

It is also to be understood that the mention of one or more method steps does not preclude the presence of additional method steps before or after the combined recited steps or intervening method steps between those steps expressly identified. Moreover, the lettering of process steps or ingredients is a convenient means for identifying discrete activities or ingredients and it is to be understood that the recited lettering can be arranged in any sequence, unless otherwise indicated.

The invention relates to processes for isolating 2,2,4,4-tetramethyl-1,3-cyclobutanediol (TMCD) by (a) crystallizing TMCD in a crystallization zone to generate a slurry comprising TMCD solids and (b) isolating TMCD solids in a solid liquid separation zone to generate a wet cake and a mother liquor. Various solvents and solvent classes have been found which allow for the recovery of TMCD solids via crystallization. In all embodiments in which one isomer of TMCD is isolated, the purity of the isolated primary isomer will be greater than 90 weight %, or greater than 95 weight %, or greater than 97 weight %, or greater than 99 weight % or greater than 99.5 weight %.

It is known in the art that crystallization is used to generate solids for the isolation and purification of desired products. In the production of TMCD, it is desirable to have a choice of different solvents to select from in order to provide options for the isolation and purification of TMCD via crystallization. We have discovered that TMCD can be crystallized and isolated from several solvent classes comprising: acetates, esters, aromatics, alcohols, ketones, water, and mixtures thereof. The solvents include alkyl acetates, alkyl propionates, alkyl carbonates, alkyl alcohols, dialkyl ketones, alkyl diols, cycloaliphatic glycols, aromatic hydrocarbons, blends of alkanes and alkyl esters, or water or mixtures thereof. Solvents may be compounds selected from any individual class of solvents including alkyl acetates, alkyl propionates, alkyl carbonates, alkyl alcohols, dialkyl ketones, alkyl diols, cycloaliphatic glycols, aromatic hydrocarbons, blends of alkanes and alkyl esters, or water or may be a combination of two or more compounds selected from two or more of the classes of solvents listed above. Preferably the alkyl acetates have alkyl groups having 1 to 8 carbon atoms and the alkyl groups may linear or branched. Preferably the alkyl propionates have alkyl groups having 1 to 8 carbon atoms, more preferably having 3-4 carbon atoms. Preferably the alkyl carbonates have alkyl groups that, independently, have 1 to 8 carbon atoms. The alkyl groups in the alkyl carbonate each independently have 1 to 8 carbon atoms, preferably 3-4 carbon atoms and may be linear or branched. Preferably the aromatic solvents have 6 to 8 carbon atoms. Preferably the alkyl alcohols have 1 to 8 carbon atoms and the alkyl group can be linear or branched. Preferable the alkyl ketones have 3 to 9 carbon atoms and the alkyl group may be linear or branched. Preferably the mixtures of alkyl acetates having 3 to 10 carbon atoms and alkanes comprise 0 to 60% alkane and 40 to 100% alkyl acetate or preferably 1 to 50% alkane and 50 to 99% alkyl acetate. Preferably the mixtures of alkyl propionates having 3 to 8 carbon atoms and alkanes having 7 to 10 carbon atoms comprise 1 to 75% alkane and 25 to 99 wt % alkyl propionate, preferably 1 to 50 wt % alkane and 99 to 50 wt % alkyl propionate. An illustrative listing of solvents includes methyl acetate, ethyl acetate, iso-butyl acetate, 2-ethylhexyl acetate, n-propyl propionate, n-butyl propionate, dimethyl carbonate, methanol, ethanol, n-butanol, 4-methyl-2-pentanol, 2-ethylhexanol, acetone, 4-methylpentan-2-one (MIBK), 2,6-dimethylheptan-4-one (DIBK), ethylene glycol, 1,4-cyclohexane dimethanol, benzene, toluene, xylene, or water or mixtures thereof. Alkanes include Isopar™ C Fluid and Isopar™ G Fluid, available from ExxonMobil Chemical Company. Isopar™ C Fluid is a branched alkane consisting primarily of eight carbon hydrocarbons. Isopar™ C Fluid comprises material identified by CAS No. 64742-66-8, also known as naphtha (petroleum) or light alkylates and by CAS No. 90622-56-3 also known as isoalkanes, C7-C10. Isopar™ G Fluid has isoalkanes as the major components. Isopar™ G Fluid comprises materials identified as CAS No. 64742-48-9 also known as hydrotreated heavy naphtha (petroleum). Isopar™ G Fluid also corresponds to EC no. 923-037-2 which is described as C10-C12 isoalkane hydrocarbons with less than 2% aromatics.

We have also discovered that the isolation of TMCD from alkanes is hindered by the tendency of the TMCD solids to nucleate on surfaces within the crystallizer (i.e. agitators, baffles, vessel walls) instead of growing as well behaved crystals in a solvent slurry. This tendency of TMCD to nucleate and grow on the vessel surfaces in alkanes demonstrates that the isolation and purification of TMCD is not a universal characteristic of all potential solvents.

For all embodiments below, the process solvent should allow for the complete dissolution and crystallization of TMCD without undesirable nucleation on the crystallizer internals. Preferably, the solvent should have a high TMCD solubility at elevated temperatures and a lower solubility at a lower temperature which allows for the recovery of TMCD from the solvent. As used herein, the term "solvent" means an individual solvent or mixture of solvents where the solvent or solvent mixture allows for the dissolution and crystallization of TMCD.

In one embodiment of the invention, the residence time is at least 0.5 hours in each zone of crystallization. Under the experimental conditions described in the Examples below, a preferred residence time of at least 0.5 hours provided good yields of crystallized product. If the residence time was much less than 0.5 hours, it is believed that there was not enough time for the material in solution to crystallize in a controlled manner due to mass transfer limitations. In one embodiment, the residence time in each crystallization zone is independently at least 0.5 hours. In another embodiment, the residence time in each crystallization zone is independently from 0.5 to four hours. In another embodiment, the residence time in each crystallization zone is independently from one to three hours.

For all embodiments below, the solid liquid separation zone comprises at least one solid liquid separation device. Examples of such solid-liquid separation devices include but are not limited to pressure filters, vacuum filters, batch pressure filters, centrifuges, decanters, and like devices. For all embodiments of the invention, all of the solid-liquid separation devices may operate in batch, semi-continuous or continuous modes. For all embodiments of the invention having more than one separation device, the solid-liquid separation devices each independently may operate in batch, semi-continuous or continuous modes.

For all embodiments below, stream 100 may be generated from the hydrogenation of 2,2,4,4-tetramethyl-1,3-cyclobutanedione to TMCD. Stream 100 comprises a process solvent and, typically, a mixture of cis- and trans-TMCD wherein the concentration of TMCD ranges from 1 to 75 wt %, based on the total weight of the solvent and the TMCD. More preferably the TMCD concentration ranges from 5 to 50 wt %. In all embodiments the stream 100 may be only cis-TMCD, only trans-TMCD or a mixture of cis- and trans-TMCD. Also, it should be appreciated that other processes known in the art will produce a stream comprising TMCD dissolved in a solvent which can be purified by this invention.

Unless specified otherwise, the term "TMCD", as used herein, means cis-2,2,4,4-tetramethyl-1,3-cyclobutanediol and/or trans-2,2,4,4-tetramethyl-1,3-cyclobutanediol. The ratio of molar concentration of cis-TMCD to trans-TMCD isomers ranges from about 0.7 to about 1.0 or from about 0.9 to about 1.3 or from about 1.1 to about 1.3 or from about 0.5 to about 1.5, or from about 0.1 to about 0.9, or from about 0.01 to about 0.99. Accordingly, in one embodiment of the invention, the molar concentration of cis-TMCD and trans-TMCD isomers in the solution to be crystallized is approximately equal. However, the invention is not constrained by the molar concentration (or weight %) of cis-TMCD and trans-TMCD and is applicable to all isomer ratios (i.e. from either a pure isomer dissolved in a solvent to a cis/trans molar ratio of one).

In one embodiment, the invention relates to a process to generate TMCD solids by crystallizing from a crystallizer feed stream 100 comprising TMCD with a single product isolation of TMCD solids as shown in FIG. 1. A process to generate TMCD solids by crystallization from a crystallizer feed stream 100 comprising TMCD dissolved in a solvent that is fed to the crystallization zone 101 to generate a slurry stream 200 comprising TMCD solids. Stream 200 is fed to a solid liquid separation zone 201 to generate a mother liquor stream 300 comprising solvent and dissolved TMCD and a wet cake stream 202 comprising TMCD solids.

In crystallization zone 101, the temperature of the crystallizer or crystallizers is set such that the concentration of TMCD in the crystallizer feed stream 100 is above its saturated concentration at the operating temperature of the crystallizer, thereby generating crystal growth. The crystallization zone may include one or more crystallizers, preferably one crystallizer or more preferably two crystallizers depending on the TMCD concentration in crystallizer feed stream 100. It will be understood by one skilled in the art that each of the described embodiments in this invention, as well as any sub-parts of those embodiments, may be operated in a continuous or a non-continuous manner. Non-continuous operations include, but are not limited to, batch-wise operations, cyclical operations, and/or intermittent operations. Slurry stream 200 is transferred from crystallization zone 101 to solid liquid separation zone 201 to form a TMCD wet cake stream 202 and a mother liquor stream 300. The generation of the wet cake may take place in a single or multiple solid-liquid separation zones.

Figure 2:
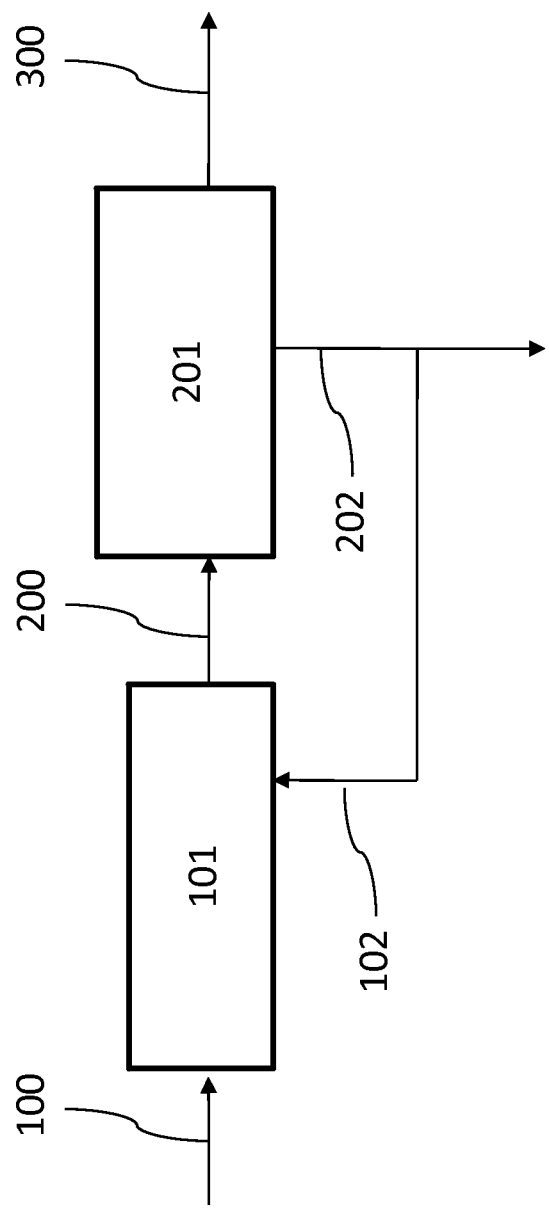
FIG. 2 is a block flow diagram of a crystallization process with a single product isolation of cis- and trans-2,2,4,4-tetramethylcyclobutane-1,3-diol and solids recycle to increase solids content in the first zone of crystallization.

In another embodiment, a process to generate TMCD solids by crystallization from a crystallizer feed stream 100 comprising TMCD with solids recycle is provided as shown in FIG. 2. Stream 100 comprising TMCD dissolved in a solvent is fed to the crystallization zone 101 to generate a slurry stream 200 comprising TMCD solids and solvent. Stream 200 is fed to a solid liquid separation zone 201 to generate a mother liquor steam 300 and a wet cake stream 202 comprising TMCD solids. A portion of the wet cake stream 202 is fed back to the crystallization zone 101 in a solids recycle stream 102. The solids recycle is included to increase solids content and/or the size of the crystals in the crystallization zone 101.

In crystallization zone 101, the temperature of the crystallizer or crystallizers is set such that the concentration of the TMCD in the crystallizer feed is above its saturated concentration at the operating temperature of the crystallizer, thereby generating crystal growth. The crystallization zone may include one or more crystallizers, preferably one crystallizer or more preferably two crystallizers depending on the TMCD concentration in crystallizer feed stream 100.

Slurry stream 200 is transferred from crystallization zone 101 to solid liquid separation zone 201 to form TMCD wet cake 202 and a mother liquor stream 300. The generation of the wet cake may take place in a single or multiple solid-liquid separation zones.

Figure 3:
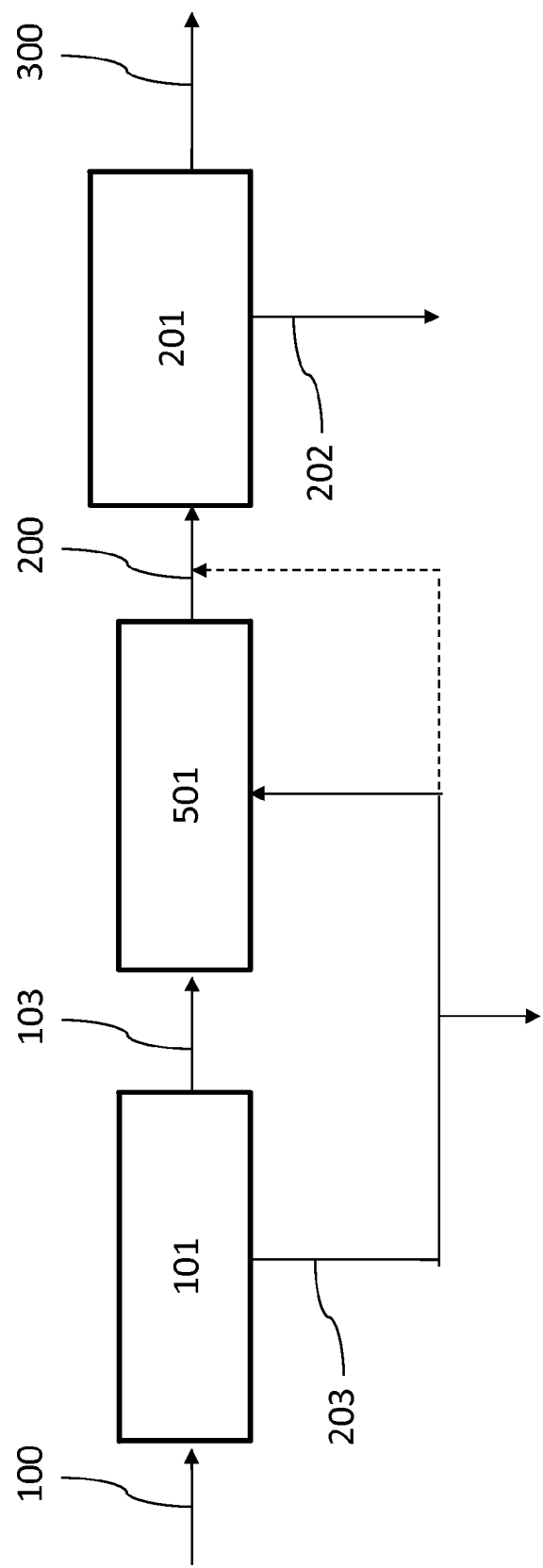
FIG. 3 is a block flow diagram of a crystallization process with a single product isolation of cis- and trans-2,2,4,4-tetramethylcyclobutane-1,3-diol with a mother liquor purge and, alternatively, partial or complete mother liquor recycle.
Figure 4:
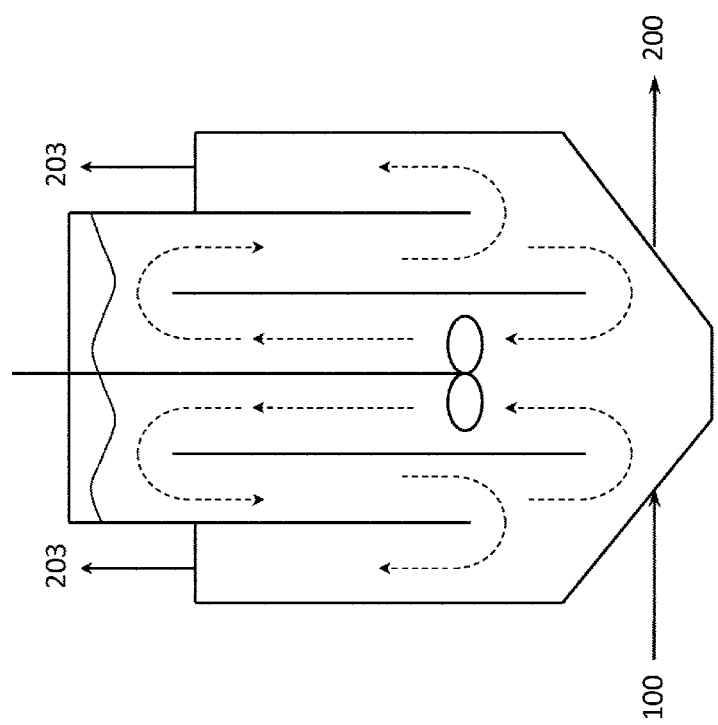
FIG. 4 is an example of a zoned crystallization system where two product streams are removed from crystallization system.

In another embodiment of the invention, a process to generate TMCD solids by crystallization from a crystallizer feed stream 100 comprising TMCD with zoned crystallizer is provided as shown in FIG. 3. Stream 100 comprising TMCD dissolved in a solvent is fed to the crystallization zone 101 to generate a slurry stream 103 comprising TMCD solids and a mother liquor stream 203. Steam 103 is fed to crystallization zone 501 to generate a second slurry stream 200. Stream 200 is fed to a solid liquid separation zone 201 to generate a mother liquor steam 300 and a wet cake stream 202 comprising TMCD solids. Stream 203 exits the process or at least a portion of stream 203 up to 100% is routed to crystallization zone 501 and/or stream 200. Crystallization zones 101 and 501 may be separate crystallizers or incorporated into the same crystallizer. The advantage of this embodiment is that the residence time of the solids produced in the zoned crystallizer 101 can be regulated separately from the residence time of the mother liquor. This method allows the solids content of the crystallizer to be controlled independent of all other operating variables relating to that zone of crystallization. This has an advantage in forming larger crystals due to the increased residence time and/or increased solids concentration. It also allows for smoother operation as the probability of heat exchanger fouling is reduced. FIG. 4 shows a zoned crystallization where two product streams are removed from a crystallization system as shown in FIG. 3.

In crystallization zone 101, the temperature of the crystallizer or crystallizers is set such that the concentration of the TMCD in the crystallizer feed is above its saturated concentration at the operating temperature of the crystallizer, thereby generating crystal growth. The crystallization zone includes at least one zoned crystallizer and may include one or more crystallizers, preferably two crystallizers depending on the TMCD concentration in stream 100.

Slurry stream 200 is transferred from crystallization zone 101 to solid liquid separation zone 201 to form a TMCD wet cake 202 and a mother liquor stream 300. The generation of the wet cake may take place in a single or multiple solid-liquid separation zones 201.

Figure 5:
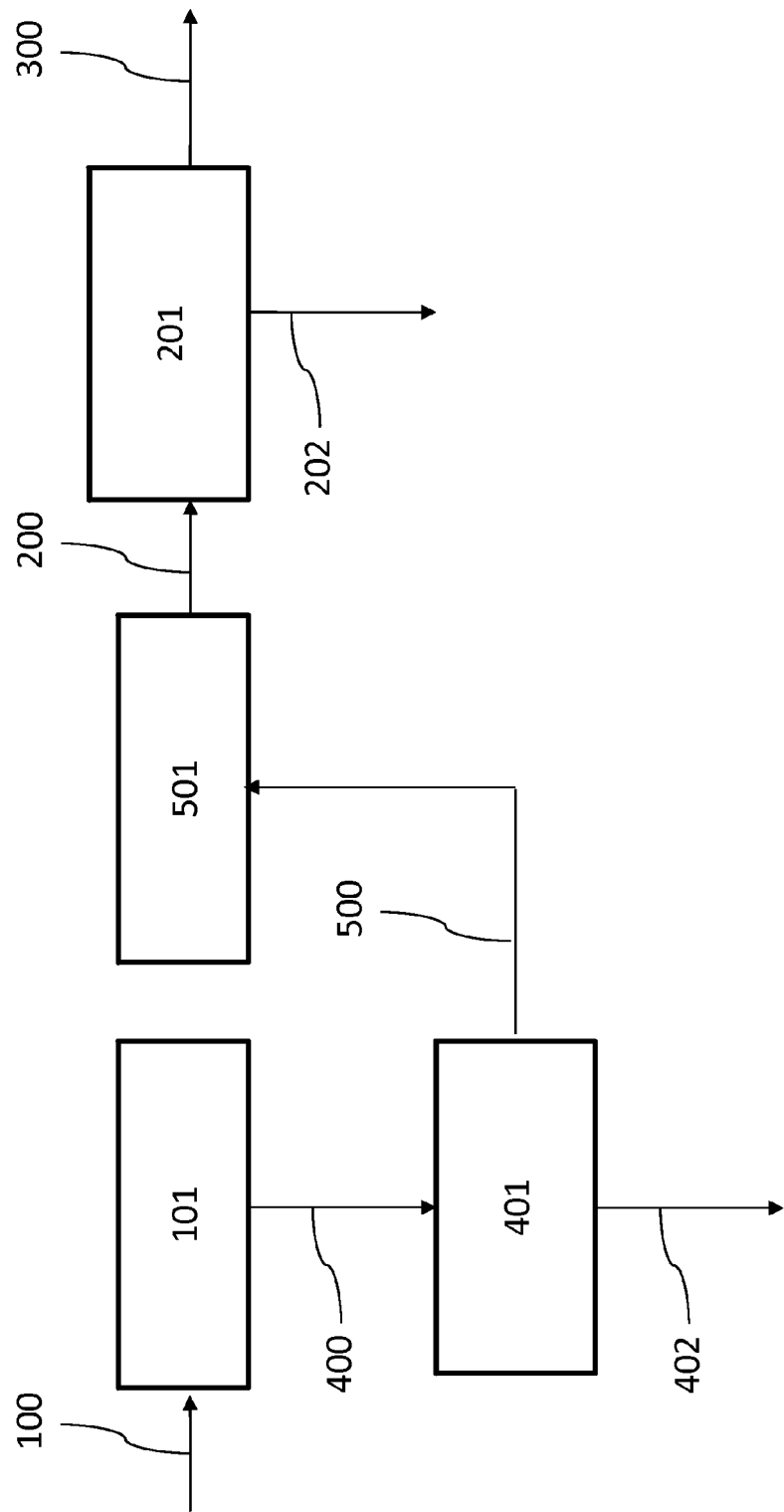
FIG. 5 is a block flow diagram of a single-zone crystallization process to isolate a single isomer of TMCD and with mother liquor recycle to a second single-zone crystallization process to isolate a mixture of cis- and trans-2,2,4,4-tetramethylcyclobutane-1,3-diol.

In another embodiment of the invention, a process to generate an isolated individual isomer TMCD solids stream and a mixed TMCD isomer solids stream by crystallization from a crystallizer feed stream 100 comprising TMCD isomers is provided as shown in FIG. 5. Stream 100 comprising mixed isomer TMCD dissolved in a solvent is fed to the crystallization zone 101 to generate a slurry stream 400 comprising single isomer TMCD solids. Stream 400 is fed to a solid liquid separation zone 401 to generate a mother liquor steam 500 and a wet cake stream 402 comprising single isomer TMCD solids. Stream 500 is fed to crystallization zone 501 to generate a slurry stream 200 comprising TMCD isomer solids. Stream 200 is fed to a solid liquid separation zone 201 to generate a mother liquor stream 300 and a wet cake stream 202 comprising mixed isomer TMCD solids.

In this embodiment, advantage can be taken of the fact that, one TMCD isomer (A) can be isolated from the other isomer depending on feed concentration and prudent selection of the temperature within crystallization zone 101. In crystallization zone 101, the temperature of the crystallizer or crystallizers is set such that the concentration of TMCD isomer (A) in the crystallizer feed is above its saturated concentration at the operating temperature of the crystallizer. The temperature must also be selected such that the concentration of TMCD isomer (B) in the crystallizer feed is below its saturated concentration at the operating temperature of the crystallizer. The crystallization zone 101 may include one or more crystallizers, preferably one crystallizer depending on the TMCD isomer concentrations in stream 100.

Slurry stream 400 is transferred from crystallization zone 101 to solid liquid separation zone 401 to form a TMCD isomer (A) wet cake 402 and a mother liquor stream 500. The generation of the wet cake may take place in a single device or multiple devices.

In crystallization zone 501, the temperature of the crystallizer or crystallizers is set such that the concentration of the TMCD in the crystallizer feed is above its saturated concentration at the operating temperature of the crystallizer, thereby generating crystal growth. The crystallization zone may include one or more crystallizers, preferably one crystallizer depending on the TMCD concentration in stream 500.

Slurry stream 200 is transferred from crystallization zone 501 to solid liquid separation zone 201 to form a TMCD wet cake 202 and a mother liquor stream 300. The generation of the wet cake may take place in a single device or multiple devices.

Figure 6:
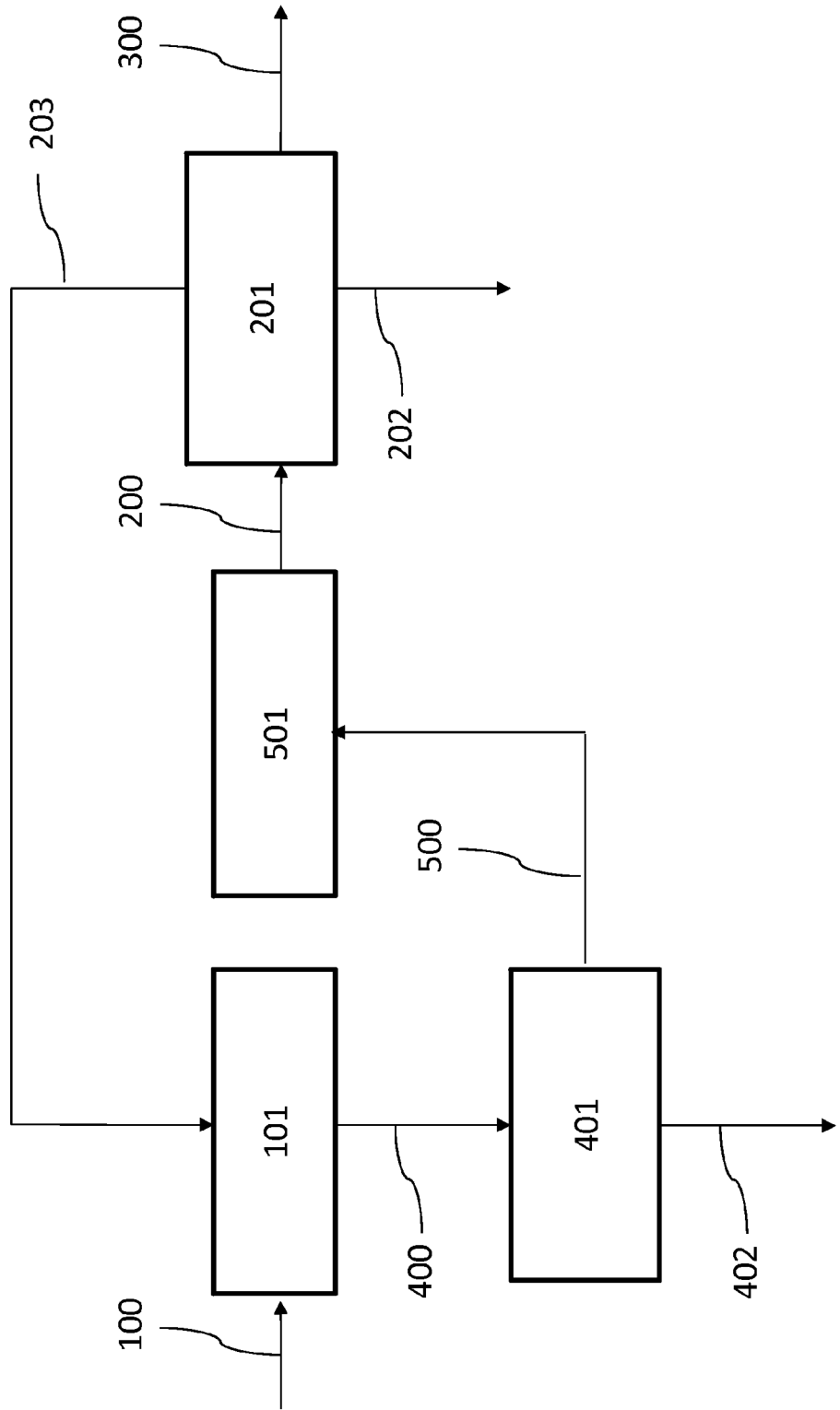
FIG. 6 is a block flow diagram of a single-zone crystallization process to isolate a single isomer of TMCD and with mother liquor recycle to a second single-zone crystallization process to isolate a mixture of cis- and trans-2,2,4,4-tetramethylcyclobutane-1,3-diol and with recycle of at least a portion of the TMCD solids to the first single-zone crystallization zone.

In another embodiment of the invention, a process to generate an isolated individual isomer TMCD solids stream and a mixed TMCD isomer solids stream by crystallization from a crystallizer feed stream 100 comprising TMCD isomers with a partial solids recycle is provided as shown in FIG. 6. Stream 100 comprising mixed isomer TMCD dissolved in a solvent is fed to the crystallization zone 101 to generate a slurry stream 400 comprising single isomer TMCD solids. Stream 400 is fed to a solid liquid separation zone 401 to generate a mother liquor steam 500 and a wet cake stream 402 comprising single isomer TMCD solids. Stream 500 is fed to crystallization zone 501 to generate a slurry stream 200 comprising TMCD isomer solids. Stream 200 is fed to a solid liquid separation zone 201 to generate a mother liquor stream 300 and a wet cake stream 202 comprising mixed isomer TMCD solids. A portion of the wet cake generated in solid liquid separation zone 201 is recycled back to crystallization zone 101 via stream 203.

In this embodiment, isolating solids at higher temperatures has advantages in terms of filtration rate and product purity. At higher temperatures, i.e., the higher temperature of the first crystallization zone relative to the lower temperature of the second crystallization zone, the mother liquor viscosity is typically lower, which allows for faster filtration times. In addition, a more pure product can be expected since impurities are typically more soluble at higher temperatures thus resulting in a more pure product.

In crystallization zone 101, the temperature of the crystallizer or crystallizers is set such that the concentration of TMCD isomer (A) in the crystallizer feed is above its saturated concentration at the operating temperature of the crystallizer. The temperature must also be selected such that the concentration of TMCD isomer (B) in the crystallizer feed is below its saturated concentration at the operating temperature of the crystallizer. The crystallization zone 101 may include one or more crystallizers, preferably one crystallizer depending on the TMCD isomer concentrations in stream 100.

Slurry stream 400 is transferred from crystallization zone 101 to solid liquid separation zone 401 to form a TMCD isomer (A) wet cake 402 and a mother liquor stream 500. The generation of the wet cake may take place in a single device or multiple devices.

In crystallization zone 501, the temperature of the crystallizer or crystallizers is set such that the concentration of the TMCD in the crystallizer feed is above its saturated concentration at the operating temperature of the crystallizer, thereby generating crystal growth. The crystallization zone may include one or more crystallizers, preferably one crystallizer depending on the TMCD concentration in stream 500.

Slurry stream 200 is transferred from crystallization zone 501 to solid liquid separation zone 201 to form a TMCD wet cake 202 and a mother liquor stream 300. The generation of the wet cake may take place in a single device or multiple devices. A portion of the wet solids produced in solid liquid separation zone 201 is recycled back to crystallizer 101 via solids recycle stream 203.

In another embodiment of the invention, a process to generate a TMCD solids stream by crystallization from a stream 100 comprising TMCD with complete solids recycle is provided as shown in FIG. 7. Stream 100 comprising TMCD dissolved in a solvent is fed to the crystallization zone 101 to generate a slurry stream 400 comprising TMCD solids. Stream 400 is fed to a solid liquid separation zone 401 to generate a mother liquor steam 500 and a wet cake stream 402 comprising TMCD solids. Stream 500 is fed to crystallization zone 501 to generate a slurry stream 200 comprising TMCD solids. Stream 200 is fed to a solid liquid separation zone 201 to generate a mother liquor stream 300. The wet cake generated in solid liquid separation zone 201 is recycled back to crystallization zone 101 via stream 203.

In this embodiment, isolating solids at higher temperatures has advantages in terms of filtration rate and product purity. At higher temperatures, i.e., the higher temperature of the first crystallization zone relative to the lower temperature of the second crystallization zone, the mother liquor viscosity is typically lower, which allows for faster filtration times. In addition, a more pure product can be expected since impurities are typically more soluble at higher temperatures thus resulting in a more pure product.

In crystallization zone 101, the temperature of the crystallizer or crystallizers is set such that the concentration of the TMCD in the crystallizer feed is above its saturated concentration at the operating temperature of the crystallizer. The crystallization zone 101 may include one or more crystallizers, preferably one crystallizer depending on the TMCD concentration in stream 100.

Slurry stream 400 is transferred from crystallization zone 101 to solid liquid separation zone 401 to form a TMCD wet cake 402 and a mother liquor stream 500. The generation of the wet cake may take place in a single device or multiple devices.

In crystallization zone 501, the temperature of the crystallizer or crystallizers is set such that the concentration of the TMCD in the crystallizer feed is above its saturated concentration at the operating temperature of the crystallizer, thereby generating crystal growth. The crystallization zone may include one or more crystallizers, preferably one crystallizer depending on the TMCD concentration in stream 500.

Slurry stream 200 is transferred from crystallization zone 501 to solid liquid separation zone 201 to form a mother liquor stream 300 and a wet solids stream 203, which is recycled back to crystallization zone 101. The generation of the wet solids may take place in a single device or multiple devices.

This invention can be further illustrated by the following examples of other embodiments thereof, although it will be understood that these examples are included merely for purposes of illustration and are not intended to limit the scope of the invention unless otherwise specifically indicated.

All concentrations were measured by gas chromatography. Water concentration was measured by Karl Fischer titrations.

Example 1

The solubility of cis-TMCD and trans-TMCD in various solvents was determined by charging cis-TMCD, trans-TMCD, and the solvent or solvents of interest into a 120 ml jacketed glass vessel. The vessel was equipped with a stir bar in order to provide mixing and the jacket was used to control the temperature of the vessel contents. The vessel was equipped with charging and sampling ports on top of the vessel.

The slurry was allowed to stand for a time sufficient for the solids to saturate the solvent at the desired temperature. At that time, a sample of the solution was withdrawn from the cell using a fritted pipette so as to remove only the liquid phase. The sample was analyzed for cis-TMCD and trans-TMCD isomer content. These values represent the saturated concentration of each isomer at the sampling temperature.

After this, the cell contents were heated to the next desired temperature and the contents were held for another time interval sufficient to allow the slurry to equilibrate. A sample was then taken of the solution and analyzed. Following this procedure, solubility data was collected up to the final desired temperature. The results for each solvent are reported in Tables 1-8.

The reported solubility of each isomer at a given temperature for a given solvent is expressed as a weight % relative to the saturated concentration of the isomer at the highest temperature reported for a given solvent.

TABLE 1

Relative Solubility of cis- and trans-TMCD in Acetates

| | Methyl Acetate (relative to 49.8° C.) | | | Ethyl Acetate (relative to 54.9° C.) | | | i-Butyl Acetate (relative to 90.1° C.) | | | 2-Ethylhexyl Acetate (relative to 79.4° C.) | | |
|---|---|---|---|---|---|---|---|---|---|---|---|---|
| Sample (#) | Temp (° C.) | Cis (relative wt %) | Trans (relative wt %) | Temp (° C.) | Cis (relative wt %) | Trans (relative wt %) | Temp (° C.) | Cis (relative wt %) | Trans (relative wt %) | Temp (° C.) | Cis (relative wt %) | Trans (relative wt %) |
| 1 | −5.0 | 9% | 9% | −5.1 | 12% | 12% | −2.5 | 5% | 5% | −5.0 | 4% | 4% |
| 2 | 5.9 | 15% | 14% | 4.2 | 15% | 16% | 4.8 | 5% | 6% | 5.9 | 5% | 6% |
| 3 | 15.5 | 22% | 22% | 15.0 | 24% | 25% | 16.9 | 8% | 9% | 15.5 | 8% | 9% |
| 4 | 25.1 | 33% | 33% | 26.2 | 37% | 38% | 25.6 | 11% | 12% | 25.1 | 12% | 12% |
| 5 | 40.5 | 59% | 59% | 40.5 | 62% | 62% | 41.3 | 19% | 21% | 40.5 | 22% | 22% |
| 6 | 49.8 | 100% | 100% | 54.9 | 100% | 100% | 56.2 | 32% | 36% | 49.8 | 31% | 32% |
| 7 | | | | | | | 70.2 | 52% | 58% | 49.9 | 32% | 33% |
| 8 | | | | | | | 90.1 | 100% | 100% | 60.5 | 47% | 48% |
| 9 | | | | | | | | | | 70.3 | 74% | 74% |
| 10 | | | | | | | | | | 79.4 | 100% | 100% |

TABLE 2

Relative Solubility of cis- and trans-TMCD in Esters

| | n-Propyl Propionate (relative to 72.2° C.) | | | n-Butyl Propionate (relative to 91.9° C.) | | | Dimethyl Carbonate (relative to 70.1° C.) | | |
|---|---|---|---|---|---|---|---|---|---|
| Sample (#) | Temp (° C.) | Cis (relative wt %) | Trans (relative wt %) | Temp (° C.) | Cis (relative wt %) | Trans (relative wt %) | Temp (° C.) | Cis (relative wt %) | Trans (relative wt %) |
| 1 | 7.0 | 10% | 11% | 6.5 | 4% | 5% | 6.2 | 7% | 7% |
| 2 | 17.1 | 14% | 15% | 16.8 | 7% | 8% | 16.3 | 9% | 9% |
| 3 | 26.7 | 21% | 22% | 27.7 | 10% | 13% | 25.7 | 14% | 14% |
| 4 | 37.4 | 30% | 29% | 41.7 | 17% | 16% | 40.5 | 28% | 27% |
| 5 | 42.4 | 34% | 37% | 41.7 | 18% | 22% | 54.7 | 55% | 54% |
| 6 | 52.2 | 50% | 53% | 52.0 | 27% | 32% | 70.1 | 100% | 100% |
| 7 | 62.9 | 72% | 76% | 61.5 | 37% | 44% | | | |
| 8 | 72.2 | 100% | 100% | 69.1 | 50% | 59% | | | |
| 9 | | | | 80.7 | 74% | 78% | | | |
| 10 | | | | 91.9 | 100% | 100% | | | |

TABLE 3

Relative Solubility of cis- and trans-TMCD in Alcohols

| Sample (#) | Methanol (relative to 41.3° C.) | | | Ethanol (relative to 60.3° C.) | | | n-Butanol (relative to 60.5° C.) | | | Methyl i-Butyl Carbinol (relative to 81.9° C.) | | | 2-Ethylhexanol (relative to 89.8° C.) | | |
|---|---|---|---|---|---|---|---|---|---|---|---|---|---|---|---|
| | Temp (° C.) | Cis (relative wt %) | Trans (relative wt %) | Temp (° C.) | Cis (relative wt %) | Trans (relative wt %) | Temp (° C.) | Cis (relative wt %) | Trans (relative wt %) | Temp (° C.) | Cis (relative wt %) | Trans (relative wt %) | Temp (° C.) | Cis (relative wt %) | Trans (relative wt %) |
| 1 | −2.5 | 77% | 70% | 5.3 | 47% | 51% | −5.0 | 41% | 39% | 9.4 | 20% | 18% | 0.7 | 10% | 11% |
| 2 | 16.9 | 86% | 82% | 14.3 | 52% | 55% | 5.9 | 46% | 44% | 20.4 | 25% | 23% | 12.5 | 16% | 15% |
| 3 | 25.6 | 91% | 89% | 25.5 | 68% | 76% | 15.5 | 51% | 49% | 31.1 | 31% | 29% | 24.7 | 21% | 20% |
| 4 | 41.3 | 100% | 100% | 39.9 | 81% | 82% | 25.1 | 59% | 58% | 40.0 | 40% | 39% | 40.0 | 29% | 28% |
| 5 | | | | 50.1 | 88% | 92% | 40.5 | 73% | 72% | 49.5 | 49% | 47% | 49.9 | 37% | 36% |
| 6 | | | | 60.3 | 100% | 100% | 49.8 | 86% | 86% | 60.0 | 62% | 60% | 60.2 | 46% | 45% |
| 7 | | | | | | | 49.9 | 86% | 86% | 69.5 | 78% | 77% | 69.3 | 58% | 57% |
| 8 | | | | | | | 60.5 | 100% | 100% | 81.9 | 100% | 100% | 79.3 | 76% | 75% |
| 9 | | | | | | | | | | | | | 89.8 | 100% | 100% |

TABLE 4

Relative Solubility of cis- and trans-TMCD in Diols

| Sample (#) | Ethylene Glycol (relative to 91.4° C.) | | | CHDM (relative to 106.9° C.) | | |
|---|---|---|---|---|---|---|
| | Temp (° C.) | Cis (relative wt %) | Trans (relative wt %) | Temp (° C.) | Cis (relative wt %) | Trans (relative wt %) |
| 1 | 16.5 | 15% | 14% | 59.5 | 12% | 45% |
| 2 | 26.5 | 25% | 24% | 69.0 | 27% | 54% |
| 3 | 36.2 | 32% | 32% | 79.2 | 58% | 74% |
| 4 | 48.5 | 42% | 44% | 88.9 | 69% | 80% |
| 5 | 61.5 | 57% | 61% | 95.6 | 85% | 91% |
| 6 | 72.1 | 68% | 68% | 106.9 | 100% | 100% |
| 7 | 82.2 | 87% | 82% | | | |
| 8 | 91.4 | 100% | 100% | | | |

TABLE 5

Relative Solubility of cis- and trans-TMCD in Ketones

| Sample (#) | Acetone (relative to 54.7° C.) | | | MIBK (relative to 80.5° C.) | | | DIBK (relative to 94.4° C.) | | |
|---|---|---|---|---|---|---|---|---|---|
| | Temp (° C.) | Cis (relative wt %) | Trans (relative wt %) | Temp (° C.) | Cis (relative wt %) | Trans (relative wt %) | Temp (° C.) | Cis (relative wt %) | Trans (relative wt %) |
| 1 | 6.2 | 28% | 27% | 15.8 | 17% | 21% | 6.2 | 5% | 5% |
| 2 | 16.3 | 37% | 36% | 26.0 | 23% | 29% | 13.3 | 6% | 7% |
| 3 | 25.7 | 51% | 50% | 35.5 | 30% | 38% | 25.2 | 9% | 10% |
| 4 | 40.5 | 73% | 72% | 50.5 | 46% | 57% | 35.1 | 12% | 13% |
| 5 | 54.7 | 100% | 100% | 61.3 | 59% | 69% | 44.1 | 16% | 18% |
| 6 | | | | 70.8 | 77% | 83% | 61.7 | 30% | 29% |
| 7 | | | | 80.5 | 100% | 100% | 71.0 | 43% | 47% |
| 8 | | | | | | | 93.9 | 97% | 95% |
| 9 | | | | | | | 94.4 | 100% | 100% |

TABLE 6

Relative Solubility of cis- and trans-TMCD in Aromatics

| Sample (#) | Benzene (relative to 70.1° C.) | | | Toluene (relative to 99.7° C.) | | | Xylenes (relative to 99.7° C.) | | |
|---|---|---|---|---|---|---|---|---|---|
| | Temp (° C.) | Cis (relative wt %) | Trans (relative wt %) | Temp (° C.) | Cis (relative wt %) | Trans (relative wt %) | Temp (° C.) | Cis (relative wt %) | Trans (relative wt %) |
| 1 | 5.6 | 3% | 3% | 15.0 | 1% | 1% | −5.1 | 1% | 0% |
| 2 | 12.7 | 3% | 3% | 26.2 | 2% | 2% | 4.2 | 0% | 0% |
| 3 | 21.2 | 6% | 6% | 40.5 | 4% | 4% | 15.0 | 1% | 1% |
| 4 | 30.9 | 10% | 10% | 54.9 | 8% | 8% | 26.2 | 1% | 2% |

TABLE 6-continued

Relative Solubility of cis- and trans-TMCD in Aromatics

| Sample (#) | Benzene (relative to 70.1° C.) | | | Toluene (relative to 99.7° C.) | | | Xylenes (relative to 99.7° C.) | | |
|---|---|---|---|---|---|---|---|---|---|
| | Temp (° C.) | Cis (relative wt %) | Trans (relative wt %) | Temp (° C.) | Cis (relative wt %) | Trans (relative wt %) | Temp (° C.) | Cis (relative wt %) | Trans (relative wt %) |
| 5 | 40.5 | 18% | 17% | 69.8 | 15% | 16% | 40.5 | 3% | 4% |
| 6 | 50.3 | 32% | 31% | 80.2 | 26% | 26% | 54.9 | 7% | 8% |
| 7 | 61.4 | 60% | 60% | 89.8 | 42% | 42% | 69.8 | 16% | 16% |
| 8 | 70.1 | 100% | 100% | 99.7 | 100% | 100% | 80.2 | 26% | 27% |
| 9 | | | | | | | 99.7 | 100% | 100% |

TABLE 7

Relative Solubility of cis- and trans-TMCD in Aromatics

| Sample (#) | n-Heptane (relative to 69.9° C.) | | | n-Decane (relative to 89.6° C.) | | |
|---|---|---|---|---|---|---|
| | Temp (° C.) | Cis (relative wt %) | Trans (relative wt %) | Temp (° C.) | Cis (relative wt %) | Trans (relative wt %) |
| 1 | 23.0 | 3% | 3% | 37.8 | 3% | 3% |
| 2 | 30.5 | 4% | 4% | 52.9 | 10% | 9% |
| 3 | 40.4 | 13% | 14% | 69.5 | 27% | 27% |
| 4 | 49.9 | 27% | 28% | 79.3 | 53% | 52% |
| 5 | 60.6 | 54% | 53% | 89.6 | 100% | 100% |
| 6 | 69.9 | 100% | 100% | | | |

TABLE 8

Relative Solubility of cis- and trans-TMCD in Water

| Sample (#) | Water (relative to 79.3° C.) | | |
|---|---|---|---|
| | Temp (° C.) | Cis (relative wt %) | Trans (relative wt %) |
| 1 | 6.2 | 52% | 38% |
| 2 | 16.3 | 55% | 38% |
| 3 | 25.7 | 51% | 35% |
| 4 | 40.5 | 50% | 39% |
| 5 | 54.7 | 56% | 50% |
| 6 | 70.1 | 79% | 73% |
| 7 | 79.3 | 100% | 100% |

Example 2

A number of batch crystallization experiments were conducted demonstrating the use of crystallization to recover cis-TMCD and trans-TMCD from various solvents. The operating conditions and feed composition for each crystallization are shown in Table 9. The batch crystallizations were conducted using a 1-L jacketed glass crystallizer with agitation. The TMCD and solvent or solvents were charged to the crystallizer and heated to the desired initial temperature to dissolve all TMCD solids. The contents were cooled at 15° C./hr until the contents in the crystallizer reached the desired final temperature. The resulting slurry was filtered on a vacuum filtration device with a 76 mm filter to isolate the TMCD solids.

In addition, Table 9 also shows the calculated cake resistance. A low value of cake resistance means that the filter cake will filter more rapidly and can be used as a standard measure of cake filtration performance. The cake resistance is defined as:

$$\text{Cake Resistance} = r = \frac{P}{u\mu L} = \frac{P}{\frac{V_f}{At}\mu L}$$

r=cake resistance (m$^{-2}$)
P=pressure drop across the cake (Pa)
u=superficial velocity of fluid through the cake (m/sec)
$\mu$=dynamic viscosity of the mother liquor (Pa·sec)
L=cake thickness (m)
$V_f$=mother liquor volume (m$^3$)
A=area of filter media (m$^2$)
t=collection time for mother liquor (sec)

In this set of experiments, it was discovered that n-heptane and n-decane did not produce a filterable slurry due to the nucleation and growth of TMCD on the inside of the vessel walls and column internals. The acetate/alkane and ester/alkane mixture examples were found to be acceptable for TMCD crystallization if the mixture was less than 50 wt % alkane.

The relative weight % ("rel wt %") results for each pure solvent in Table 9 are expressed as a weight % relative to the saturated concentration of the isomer in that solvent at the highest temperature reported for that solvent in Tables 1-8. The mixed acetate/n-heptane solvent "rel wt %" results in Table 9 are expressed as a weight % relative to the saturated concentration of the isomer in the pure acetate solvent at the highest temperature reported for that solvent in Table 1. The isobutyl isobutyrate (IBIB)/n-heptane solvent "rel wt %" results in Table 9 are expressed as a weight % relative to the saturated concentration of the isomer in pure ethyl acetate solvent at the highest temperature reported in Table 1.

TABLE 9

| Solvent | | Feed | | Temp | | | ML | | | Wet Solids | | | Cake |
|---|---|---|---|---|---|---|---|---|---|---|---|---|---|
| Class | Name | c-TMCD | t-TMCD | Initial | Final | Slurry | total | c-TMCD | t-TMCD | total | c-TMCD | t-TMCD | Yield | Resistance |
| | | (relative wt %) | | (° C.) | (° C.) | (g) | (g) | (relative wt %) | | (g) | (absolute wt %) | | (%) | (m$^{-2}$) |
| Acetate | Methyl Acetate | 96.9% | 74.7% | 56 | 10 | 770 | 591 | 20.8% | 20.4% | 150 | 53.8% | 55.1% | 95.6 | 7.56E+10 |

TABLE 9-continued

| | | Feed | | Temp | | | ML | | | Wet Solids | | | Cake |
|---|---|---|---|---|---|---|---|---|---|---|---|---|---|
| | Solvent | c-TMCD | t-TMCD | Initial | Final | Slurry | total | c-TMCD | t-TMCD | total | c-TMCD | t-TMCD | Yield | Resistance |
| Class | Name | (relative wt %) | | (° C.) | (° C.) | (g) | (g) | (relative wt %) | | (g) | (absolute wt %) | | (%) | (m$^{-2}$) |
| Acetate | Ethyl Acetate | 139.4% | 62.9% | 70 | 10 | 650 | 535 | 22.0% | 22.5% | 103 | 50.1% | 48.8% | 77.2 | 1.10E+11 |
| Acetate | i-Butyl Acetate | 77.0% | 36.1% | 90 | 10 | 881 | 609 | 6.4% | 7.7% | 181 | 64.3% | 33.4% | 92.1 | 1.31E+11 |
| Acetate | 2-Ethyl-hexyl Acetate | 151.0% | 88.3% | 96 | 10 | 778 | 584 | 8.0% | 8.3% | 180 | 56.5% | 31.7% | 95.6 | 6.82E+10 |
| Ester | n-Propyl Propionate | 131.2% | 61.1% | 82 | 10 | 701 | 525 | 12.0% | 13.0% | 162 | 68.5% | 22.6% | 96.3 | 4.65E+10 |
| Alcohol | Methanol | 107.5% | 74.8% | 60 | 0 | 91 | 72 | 81.5% | 76.6% | 13 | 67.0% | 30.7% | 27.4 | 1.59E+12 |
| Alcohol | n-Butanol | 103.5% | 52.2% | 57 | 10 | 784 | 688 | 51.8% | 56.6% | 83 | 89.4% | 3.9% | 34.9 | 5.12E+11 |
| Alcohol | 2-Ethyl-hexanol | 79.0% | 36.5% | 84 | 10 | 426 | 303 | 19.2% | 18.0% | 109 | 48.6% | 21.0% | 78.7 | 1.41E+12 |
| Diol | EG | 76.3% | 52.7% | 94 | 10 | 75 | 40 | 17.9% | 17.2% | 32 | 35.2% | 25.5% | 74.0 | 2.92E+10 |
| Diol | CHDM | 78.4% | 39.4% | 93 | 65 | 34 | 26 | 53.0% | 44.3% | 3 | 83.1% | 3.4% | 22.5 | — |
| Ketone | Acetone | 104.5% | 44.8% | 52 | 10 | 799 | 643 | 34.1% | 33.5% | 135 | 88.1% | 16.9% | 65.0 | 5.13E+10 |
| Ketone | MIBK | 94.5% | 59.3% | 93 | 10 | 75 | 54 | 16.5% | 21.2% | 16 | 60.7% | 38.1% | 82.9 | 8.55E+10 |
| Ketone | DIBK | 62.4% | 27.5% | 90 | 10 | 744 | 627 | 5.4% | 6.2% | 109 | 72.1% | 22.9% | 88.7 | 7.44E+10 |
| Aromatic | Toluene | 82.6% | 43.3% | 105 | 10 | 838 | 670 | 0.6% | 0.6% | 153 | 55.8% | 43.7% | 103.7 | * |
| Alkane | n-Heptane | — | — | 90 | 10 | — | — | — | — | — | — | — | — | — |
| Alkane | n-Decane | — | — | 108 | 40 | — | — | — | — | — | — | — | — | — |
| Water | Water | 45.6% | 68.7% | 80 | 10 | 939 | 890 | 34.5% | 37.6% | 34 | 26.1% | 62.3% | 39.8 | 9.45E+10 |
| Mixed | Ethyl Acetate/ n-Heptane (50/50) | 61.2% | 25.6% | 74 | 10 | 723 | 655 | 7.4% | 8.0% | 54 | 50.8% | 50.7% | 87.8 | 9.96E+10 |
| Mixed | i-Butyl Acetate/ n-Heptane (75/25) | 42.5% | 19.3% | 82 | 10 | 770 | 672 | 4.5% | 5.3% | 85 | 55.8% | 41.3% | 90.1 | 7.86E+10 |
| Mixed | IBIB/n-Heptane (50/50) | 23.2% | 27.0% | 85 | 10 | 574 | 533 | 1.9% | 2.0% | 32 | 34.9% | 63.9% | 98.2 | * |

An attempt was made to collect data for cake resistance calculations, but the filtration rate was too fast to accurately measure collection of the filtrate.

Example 3

The term "semi-continuous," as used herein, describes a process where there is an intermittent feed to one or more crystallizers and an intermittent product stream discharge. From the information described in the specification and these Examples, one of skill in the art would be able to design a batch or a continuous crystallization process.

Semi-continuous experiments were conducted demonstrating the use of a continuous crystallization process to isolate and purify TMCD solids from a solution comprising TMCD. The crystallization process consisted of a feed tank and two crystallizers followed by vacuum filtration to isolate the TMCD solids from the crystallizer slurry. The experimental set-up comprised a 12 liter jacketed feed vessel, an FMI pump with heat tape traced transfer lines, two 4 liter jacketed vessels with pitched blade impellers (with a diameter ~40% of the vessel I.D.), three heating/cooling baths, two condensers, and a nitrogen purge for each vessel. Crystallizer 2 had an additional A310 impeller located at ~ the 2 liter level on the stirrer shaft. Prior to starting continuous operation, ~2 liters of material were charged to the crystallizers and a four hour batch cool down was completed to reach the desired operating temperatures and generate the necessary level of slurry. The feed was transferred to the first crystallizer (C1) continuously using an FMI pump. Slurry was transferred semi-continuously from C1 to crystallizer 2 (C2) every 30 minutes using vacuum. Dip tubes were installed in each crystallizer to control the levels and provide consistent sample volumes during transfers. Slurry was collected every 30 minutes from crystallizer 2 (C2) for filtration. The operating volume for each crystallizer was between 1.5 to 2.5 liters with 1000 ml of material transferred between crystallizers and removed from crystallizer 2 for filtration.

The feed rate to crystallizer 1 was ~33 ml/min. Once continuous operation was started, the first four transfers of slurry were disposed of before providing material for filtration experiments. Filtration experiments were completed using a 76 mm fritted filter at 20" Hg vacuum with qualitative grade filter paper. Specific operational conditions and results for each evaluated solvent are shown in Table 10.

In addition, Table 10 also shows the calculated cake resistance and specific cake resistance. A low value of cake resistance means that the filter cake will filter more rapidly and can be used as a standard measure of cake filtration performance. As noted in W. Leu, Principles of Compressible Cake Filtration, in Encyclopedia of Fluid Mechanics, Volume 5, (N. P. Cheremisinoff, ed), Gulf, 1986, specific cake resistance values of $10^9$ m/kg, $10^{10}$ m/kg, $10^{11}$ m/kg, $10^{12}$ m/kg and $10^{13}$ m/kg correspond to ease of separation of very easy, easy, moderate, difficult and very difficult, respectively. The specific cake resistance is defined as:

$$\text{Specific Cake Resistance} = \alpha = \frac{2mPA^2}{\mu X_s} = \frac{2mPA^2}{\mu\left(\frac{m_c X_c}{V_f}\right)}$$

α=specific cake resistance (m/kg)
P=pressure drop across the cake (Pa)
μ=dynamic viscosity of the mother liquor (Pa·sec)
$V_f$=mother liquor volume (m³)
A=area of filter media (m²)
m=slope of line from $t/V_f$ vs $V_f$ plot (sec/m⁶)
$X_s$=mass of dry solids in cake per volume of filtrate (kg/m³)
$m_c$=mass of wet cake (kg)
$X_c$=mass fraction of solids in the cake (kg/kg)

In this set of experiments, it was discovered that IBIB mixtures with n-heptane with alkane concentrations greater than 57% did experience nucleation and growth of TMCD on the inside of the vessel walls during the initial start-up cool down procedure. It was also discovered that IBIB mixtures with n-heptane with alkane concentrations of 70% did not result in a feasible TMCD crystallization solvent for similar reasons. Seeding of the mixture did improve the crystallization operation allowing the production of a filterable TMCD slurry with a 70% n-heptane concentration.

The "relative wt %" results for each pure solvent in Table 10 are expressed as a weight % relative to the saturated concentration of the isomer in that solvent at the highest temperature reported for that solvent in Tables 1-8. The mixed iso-butyl acetate/n-heptane solvent "relative wt %" results in Table 10 are expressed as a weight % relative to the saturated concentration of the isomer in pure iso-butyl acetate solvent at the highest temperature reported for that solvent in Table 1. The IBIB/n-heptane solvent "relative wt %" results in Table 10 are expressed as a weight % relative to the saturated concentration of the isomer in pure ethyl acetate solvent at the highest temperature reported in Table 1.

TABLE 10

| Solvent | | Feed | | Feed Temp | C1 Temp | C2 Temp | Slurry | ML | | |
|---|---|---|---|---|---|---|---|---|---|---|
| Class | Name | c-TMCD | t-TMCD | | | | | total | c-TMCD | t-TMCD |
| | | (relative wt %) | | (° C.) | (° C.) | (° C.) | (g) | (g) | (relative wt %) | |
| Acetate | Ethyl Acetate | 156.7 | 64.2 | 78 | 40 | 15 | 764 | 634 | 25.6 | 25.9 |
| Acetate | 2-Ethylhexyl Acetate | 125.1 | 50.4 | 78 | 40 | 15 | 995 | 815 | 9.0 | 9.1 |
| Alcohol | Ethanol | 98.6 | 79.7 | 65 | 30 | 15 | 907 | 772 | 69.5 | 79.1 |
| Alcohol | 2-Ethylhexanol | 60.8 | 39.0 | 78 | 40 | 15 | 778 | 585 | 21.5 | 22.1 |
| Ketone | MIBK | 55.8 | 40.8 | 65 | 40 | 15 | 714 | 628 | 16.1 | 20.3 |
| Mixed | i-Butyl Acetate/n-Heptane (50/50) | 22.6 | 14.5 | 80 | 45 | 15 | 849 | 775 | 2.4 | 2.8 |
| Mixed | IBIB/n-Heptane (30/70) | 33.4 | 14.7 | 92 | 60 | 30 | 915 | 845 | 1.8 | 1.8 |
| Mixed | IBIB/n-Heptane (43/57) | 34.1 | 18.0 | 92 | 60 | 30 | 1004 | 944 | 3.9 | 4.0 |

| Solvent | | Wet Solids | | | Yield | Cake Resistance | Specific Cake Resistance |
|---|---|---|---|---|---|---|---|
| Class | Name | total (g) | c-TMCD | t-TMCD | % | (m⁻²) | (m/kg) |
| | | | (relative wt %) | | | | |
| Acetate | Ethyl Acetate | 120 | 45.7% | 37.1% | 59.2 | 1.59E+11 | 5.82E+10 |
| Acetate | 2-Ethylhexyl Acetate | 166 | 60.1% | 27.4% | 96.6 | 3.87E+10 | 7.93E+09 |
| Alcohol | Ethanol | 117 | 87.3% | 9.5% | 30.5 | 1.44E+11 | 4.98E+10 |
| Alcohol | 2-Ethylhexanol | 183 | 35.4% | 22.1% | 67.5 | 2.10E+11 | 1.39E+11 |
| Ketone | MIBK | 77 | 67.9% | 29.6% | 67.1 | 8.15E+10 | * |
| Mixed | i-Butyl Acetate/n-Heptane (50/50) | 53 | 57.9% | 47.3% | 90.0 | 6.16E+10 | * |
| Mixed | IBIB/n-Heptane (30/70) | 24 | 58.1% | 41.3% | 53.6 | 9.35E+10 | * |
| Mixed | IBIB/n-Heptane (43/57) | 40 | 57.3% | 40.1% | 73.8 | 3.68E+10 | * |

In the drawings and specification, there have been disclosed typical preferred embodiments of the invention and, although specific terms are employed, they are used in a generic and descriptive sense only and not for purposes of limitation, the scope of the invention being set forth in the following claims.

We claim:

1. A process for the crystallization from a mixture comprising cis-2,2,4,4-tetramethylcyclobutanediol and trans-2,2,4,4-tetramethylcyclobutanediol dissolved in a solvent, the process comprising:
    (a) crystallizing at least a portion of 2,2,4,4-tetramethylcyclobutanediol in a crystallization zone operated at a temperature such that the concentration of 2,2,4,4-tetramethylcyclobutanediol in the crystallization zone is above the saturated concentration of 2,2,4,4-tetramethylcyclobutanediol to form a slurry comprising crystallized 2,2,4,4-tetramethylcyclobutanediol and the solvent;
    (b) transferring the slurry to a solid-liquid separation zone,
    (c) separating the slurry into a mother liquor stream comprising the solvent and dissolved 2,2,4,4-tetramethylcyclobutanediol and into a wet cake stream comprising at least a portion of the crystallized 2,2,4,4-tetramethylcyclobutanediol;
wherein the solvent comprises an alkyl acetate, an alkyl propionate, an alkyl carbonate, an alkyl alcohol, an aromatic hydrocarbon, an alkyl ketone, an alkyl glycol, a blend of (1) an alkyl hydrocarbon and (2) an alkyl ester, or water or mixtures thereof.

2. The process according to claim 1, wherein at least a portion of the wet cake is returned to the crystallization zone.

3. The process of claim 1, wherein the solvent comprises an alkyl acetate with the alkyl group having 1 to 8 carbon atoms, an alkyl propionate with the alkyl group having 1 to 8 carbon atoms, an alkyl carbonate with the alkyl groups independently having 1 to 8 carbon atoms, an alkyl alcohol with the alkyl group having 1 to 8 carbon atoms, an aromatic hydrocarbon having 6 to 8 carbon atoms, an alkyl ketone with the alkyl groups independently having 1 to 8 carbon atoms, an alkyl glycol having 2 to 8 carbon atoms, a blend of (1) 1 to 75 weight % of an alkyl hydrocarbon having 5 to 10 carbon atoms and (2) 25 to 99 weight % of an alkyl ester having 2 to 8 carbon atoms, or water or mixtures thereof.

4. The process of claim 1, wherein the solvent comprises methyl acetate, ethyl acetate, iso-butyl acetate, 2-ethylhexyl acetate, n-propyl propionate, n-butyl propionate, dimethyl carbonate, methanol, ethanol, n-butanol, 4-methyl-2-pentanol, 2-ethylhexanol, acetone, 4-methylpentan-2-one, 2,6-dimethylheptan-4-one, ethylene glycol, 1,4-cyclohexane dimethanol, benzene, toluene, xylene, a blend of (1) primarily C8 hydrocarbons and (2) an alkyl ester having 2 to 8 carbon atoms, a blend of (1) primarily C10 to C12 isoalkane hydrocarbons and (2) an alkyl ester having 2 to 8 carbon atoms, or water or mixtures thereof.

5. The process of claim 2, wherein the solvent comprises an alkyl acetate with the alkyl group having 1 to 8 carbon atoms, an alkyl propionate with the alkyl group having 1 to 8 carbon atoms, an alkyl carbonates with the alkyl groups independently having 1 to 8 carbon atoms, an alkyl alcohol with the alkyl group having 1 to 8 carbon atoms, an aromatic hydrocarbon having 6 to 8 carbon atoms, an alkyl ketone with the alkyl groups independently having 1 to 8 carbon atoms, an alkyl glycol having 2 to 8 carbon atoms, a blend of (1) 1 to 75 weight % of an alkyl hydrocarbon having 5 to 10 carbon atoms and (2) 25 to 99 weight % of an alkyl ester having 2 to 8 carbon atoms, or water, or mixtures thereof.

6. The process of claim 2, wherein the solvent comprises methyl acetate, ethyl acetate, iso-butyl acetate, 2-ethylhexyl acetate, n-propyl propionate, n-butyl propionate, dimethyl carbonate, methanol, ethanol, n-butanol, 4-methyl-2-pentanol, 2-ethylhexanol, acetone, 4-methylpentan-2-one, 2,6-dimethylheptan-4-one, ethylene glycol, 1,4-cyclohexane dimethanol, benzene, toluene, xylene, a blend of primarily C8 hydrocarbons and an alkyl ester having 2 to 8 carbon atoms, a blend of (1) primarily C10 to C12 isoalkane hydrocarbons and (2) an alkyl ester having 2 to 8 carbon atoms, or water, or mixtures thereof.

7. A process for the crystallization from a mixture comprising cis-2,2,4,4-tetramethylcyclobutanediol and trans-2,2,4,4-tetramethylcyclobutanediol dissolved in a solvent, the process comprising:
    (a) crystallizing at least a portion of one of the 2,2,4,4-tetramethylcyclobutanediol isomers in the crystallization zone which is operated at a temperature such that the concentration of the crystallized 2,2,4,4-tetramethylcyclobutanediol isomer is above its saturated concentration and the other isomer concentration is below its saturated concentration to form a slurry of the crystallized isomer,
    (b) transferring the slurry to the solid-liquid separation zone, wherein at least a portion of the slurry is separated into a mother liquor stream comprising the solvent and dissolved 2,2,4,4-tetramethylcyclobutanediol and into a wet cake stream comprising at least a portion of the crystallized isomer of 2,2,4,4-tetramethylcyclobutanediol, wherein the crystallized isomer of 2,2,4,4-tetramethylcyclobutanediol comprises at least 90 weight % of one isomer, based on the total weight of the crystallized 2,2,4,4-tetramethylcyclobutanediol,
wherein the solvent comprises an alkyl acetate, an alkyl propionate, an alkyl carbonate, an alkyl alcohol, an aromatic hydrocarbon, an alkyl ketone, an alkyl glycol, a blend of (1) an alkyl hydrocarbon and (2) an alkyl ester, or water or mixtures thereof.

8. The process according to claim 7, wherein the crystallized isomer of 2,2,4,4-tetramethylcyclobutanediol has less than 5 weight % of the other isomer.

9. The process according to claim 7, wherein the crystallized isomer of 2,2,4,4-tetramethylcyclobutanediol is cis-2,2,4,4-tetramethylcyclobutanediol.

10. The process of claim 7, wherein the crystallized isomer of 2,2,4,4-tetramethylcyclobutanediol is trans-2,2,4,4-tetramethylcyclobutanedio.

11. The process according to claim 7, wherein at least a portion of the wet cake is returned to the crystallization zone.

12. The process of claim 7, wherein the solvent comprises an alkyl acetate with the alkyl group having 1 to 8 carbon atoms, an alkyl propionate with the alkyl group having 1 to 8 carbon atoms, an alkyl carbonate with the alkyl groups independently having 1 to 8 carbon atoms, an alkyl alcohol with the alkyl group having 1 to 8 carbon atoms, an aromatic hydrocarbon having 6 to 8 carbon atoms, an alkyl ketone with the alkyl groups independently having 1 to 8 carbon atoms, an alkyl glycol having 2 to 8 carbon atoms, a blend of (1) 1 to 75 weight % of an alkyl hydrocarbon having 5 to 10 carbon atoms and (2) 25 to 99 weight % of an alkyl ester having 2 to 8 carbon atoms, or water or mixtures thereof.

13. The process of claim 7, wherein the solvent comprises methyl acetate, ethyl acetate, iso-butyl acetate, 2-ethylhexyl acetate, n-propyl propionate, n-butyl propionate, dimethyl carbonate, methanol, ethanol, n-butanol, 4-methyl-2-pentanol, 2-ethylhexanol, acetone, 4-methylpentan-2-one, 2,6-dimethylheptan-4-one, ethylene glycol, 1,4-cyclohexane dimethanol, benzene, toluene, xylene, a blend of primarily C8 hydrocarbons and an alkyl ester having 2 to 8 carbon atoms, a blend of (1) primarily C10 to C12 isoalkane hydrocarbons and (2) an alkyl ester having 2 to 8 carbon atoms, or water or mixtures thereof.

14. The process of claim 11, wherein the solvent comprises an alkyl acetate with the alkyl group having 1 to 8 carbon atoms, an alkyl propionate with the alkyl group having 1 to 8 carbon atoms, an alkyl carbonate with the alkyl groups independently having 1 to 8 carbon atoms, an alkyl alcohol with the alkyl group having 1 to 8 carbon atoms, an aromatic hydrocarbon having 6 to 8 carbon atoms, an alkyl ketone with the alkyl groups independently having 1 to 8 carbon atoms, an alkyl glycol having 2 to 8 carbon atoms, a blend of (1) 1 to 75 weight % of an alkyl hydrocarbon having 5 to 10 carbon atoms and (2) 25 to 99 weight % of an alkyl ester having 2 to 8 carbon atoms, or water, or mixtures thereof.

15. The process of claim 11, wherein the solvent comprises methyl acetate, ethyl acetate, iso-butyl acetate, 2-ethylhexyl acetate, n-propyl propionate, n-butyl propionate, dimethyl carbonate, methanol, ethanol, n-butanol, 4-methyl-2-pentanol, 2-ethylhexanol, acetone, 4-methylpentan-2-one, 2,6-dimethylheptan-4-one, ethylene glycol, 1,4-cyclohexane dimethanol,
   benzene, toluene, xylene, a blend of primarily C8 hydrocarbons and an alkyl ester having 2 to 8 carbon atoms, a blend of (1) primarily C10 to C12 isoalkane hydrocarbons and (2) an alkyl ester having 2 to 8 carbon atoms, or water, or mixtures thereof.

16. A process for the crystallization from a mixture comprising cis-2,2,4,4-tetramethylcyclobutanediol and trans-2,2,4,4-tetramethylcyclobutanediol dissolved in a solvent, the process comprising:
   (a) crystallizing at least a portion of 2,2,4,4-tetramethylcyclobutanediol in a first crystallization zone operated at a temperature such that the concentration of 2,2,4,4-tetramethylcyclobutanediol in the first crystallization zone is above the saturated concentration of 2,2,4,4-tetramethylcyclobutanediol to form a first slurry comprising crystallized 2,2,4,4-tetramethylcyclobutanediol and the solvent,
   (b) transferring at least a portion of the first slurry to a second crystallization zone independently from the transfer of at least a portion of a first mother liquor from the first crystallization zone to the second crystallization zone,
   (c) crystallizing at least a second portion of 2,2,4,4-tetramethylcyclobutanediol in the second crystallization zone operated at a temperature such that the concentration of 2,2,4,4-tetramethylcyclobutanediol in the second crystallization zone is above the saturated concentration of 2,2,4,4-tetramethylcyclobutanediol to form a second slurry comprising the second portion of 2,2,4,4-tetramethylcyclobutanediol and the solvent,
   (d) transferring the second slurry to a solid-liquid separation zone,
   (e) separating the second slurry into a second portion of mother liquor stream comprising the solvent and the dissolved 2,2,4,4-tetramethylcyclobutanediol and into a wet cake stream comprising the second portion of crystallized 2,2,4,4-tetramethylcyclobutanediol;
wherein the solvent comprises an alkyl acetate, an alkyl propionate, an alkyl carbonate, an alkyl alcohol, an aromatic hydrocarbon, an alkyl ketone, an alkyl glycol, a blend of (1) an alkyl hydrocarbon and (2) an alkyl ester, or water or mixtures thereof.

17. The process of claim 16, wherein the solvent comprises an alkyl acetate with the alkyl group having 1 to 8 carbon atoms, an alkyl propionate with the alkyl group having 1 to 8 carbon atoms, an alkyl carbonate with the alkyl groups independently having 1 to 8 carbon atoms, an alkyl alcohol with the alkyl group having 1 to 8 carbon atoms, an aromatic hydrocarbon having 6 to 8 carbon atoms, an alkyl ketone with the alkyl groups independently having 1 to 8 carbon atoms, an alkyl glycol having 2 to 8 carbon atoms, a blend of (1) 1 to 75 weight % of an alkyl hydrocarbon having 5 to 10 carbon atoms and (2) 25 to 99 weight % of an alkyl ester having 2 to 8 carbon atoms, or water, or mixtures thereof.

18. The process of claim 16, wherein the solvent comprises methyl acetate, ethyl acetate, iso-butyl acetate, 2-ethylhexyl acetate, n-propyl propionate, n-butyl propionate, dimethyl carbonate, methanol, ethanol, n-butanol, 4-methyl-2-pentanol, 2-ethylhexanol, acetone, 4-methylpentan-2-one, 2,6-dimethylheptan-4-one, ethylene glycol, 1,4-cyclohexane dimethanol, benzene, toluene, xylene, a blend of (1) primarily C8 hydrocarbons and (2) an alkyl ester having 2 to 8 carbon atoms, a blend of primarily (1) C10 to C12 isoalkane hydrocarbons and (2) an alkyl ester having 2 to 8 carbon atoms, or water, or mixtures thereof.

19. A process for the crystallization from a mixture comprising cis-2,2,4,4-tetramethylcyclobutanediol and trans-2,2,4,4-tetramethylcyclobutanediol dissolved in a solvent, the process comprising:
   (a) crystallizing at least a portion of one of the 2,2,4,4-tetramethylcyclobutanediol isomers in the first crystallization zone which is operated at a temperature such that the feed concentration of one of the isomers is above its saturated concentration and the other isomer feed concentration is below its saturated concentration to form a first slurry of comprising at least 90 weight % of one crystallized isomer, based on the total weigh of crystallized isomers,
   (b) transferring the first slurry from the first crystallization zone to the second crystallization zone independently from the transfer of at least a portion of a first mother liquor from the first crystallization zone to the second crystallization zone,
   (c) crystallizing at least a second portion of one of the 2,2,4,4-tetramethylcyclobutanediol isomers in a second crystallization zone which is operated at a temperature such that the feed concentration of one of the isomers is above its saturated concentration and the other isomer is below its saturated concentration to form a second slurry comprising at least 90 weight % of the crystallized isomer, based on the total weight of the crystallized isomers;
   (d) transferring the second slurry to a solid-liquid separation zone, wherein the second slurry is separated into a second mother liquor stream comprising the solvent and the dissolved 2,2,4,4-tetramethylcyclobutanediol and into a wet cake stream comprising at least 90 weight % of the crystallized isomer of 2,2,4,4-tetramethylcyclobutanediol, based on the total weight of the crystallized isomers, of 2,2,4,4-tetramethylcyclobutanediol.

20. The process of claim 19, wherein the solvent comprises an alkyl acetate with the alkyl group having 1 to 8 carbon atoms, an alkyl propionate with the alkyl group having 1 to 8 carbon atoms, an alkyl carbonate with the alkyl groups independently having 1 to 8 carbon atoms, an alkyl alcohol with the alkyl group having 1 to 8 carbon atoms, an aromatic hydrocarbon having 6 to 8 carbon atoms, an alkyl ketone with the alkyl groups independently having 1 to 8 carbon atoms, an alkyl glycol having 2 to 8 carbon atoms, a blend of (1) 1 to 75 weight % of an alkyl hydrocarbon having 5 to 10 carbon atoms and (2) 25 to 99 weight % of an alkyl ester having 2 to 8 carbon atoms, or water, or mixtures thereof.

21. The process of claim 19, wherein the solvent comprises methyl acetate, ethyl acetate, iso-butyl acetate, 2-ethylhexyl acetate, n-propyl propionate, n-butyl propionate, dimethyl carbonate, methanol, ethanol, n-butanol, 4-methyl-2-pentanol, 2-ethylhexanol, acetone, 4-methylpentan-2-one, 2,6-dimethylheptan-4-one, ethylene glycol, 1,4-cyclohexane dimethanol, benzene, toluene, xylene, a blend of primarily C8 hydrocarbons and an alkyl ester having 2 to 8 carbon atoms, a blend of primarily (1) C10 to C12 isoalkane hydrocarbons and (2) an alkyl ester having 2 to 8 carbon atoms, or water, or mixtures thereof.

22. A process for the crystallization of a mixture comprising cis-2,2,4,4-tetramethylcyclobutanediol and trans-2,2,4,4-tetramethylcyclobutanediol dissolved in a solvent, the process comprising:
   (a) crystallizing at least a portion of one of the 2,2,4,4-tetramethylcyclobutanediol isomers in the first crystallization zone which is operated at a temperature such that the feed concentration of one of the isomers is above its saturated concentration and the other isomer feed concentration is below its saturated concentration to form a first slurry of comprising at least 90 weight % of one crystallized isomer, based on the total weight of crystallized isomers;
   (b) transferring the first slurry to a solid liquid separation zone wherein the first slurry is separated into a first mother liquor stream comprising the solvent and the dissolved 2,2,4,4-tetramethylcyclobutanediol and into a first wet cake stream comprising at least a portion of the crystallized isomer of 2,2,4,4-tetramethylcyclobutanediol;
   (c) transferring the first mother liquor stream to a second crystallization zone wherein both 2,2,4,4-tetramethylcyclobutanediol isomers are crystallized to form a second slurry comprising cis- and trans-2,2,4,4-tetramethylcyclobutanediol and the solvent;
   (d) transferring the second slurry to a second solid liquid separation zone,
   (e) separating the second slurry into a second mother liquor stream comprising the solvent and the dissolved 2,2,4,4-tetramethylcyclobutanediol and into a second wet cake stream comprising the crystallized cis- and trans-2,2,4,4-tetramethylcyclobutanediol; wherein the solvent comprises an alkyl acetate, an alkyl propionate, an alkyl alcohol, an aromatic hydrocarbon, an alkyl ketone, an alkyl glycol, a blend of (1) an alkyl hydrocarbon and (2) an alkyl ester, or water or mixtures thereof.

23. The process according to claim 22, further comprising: transferring at least a portion of the second wet cake comprising solid cis-2,2,4,4-tetramethylcyclobutanediol and solid trans-2,2,4,4-tetramethylcyclobutanediol from the second solid liquid separation zone to the first crystallization zone.

24. The process of claim 22, wherein the solvent comprises an alkyl acetate with the alkyl group having 1 to 8 carbon atoms, an alkyl propionate with the alkyl group having 1 to 8 carbon atoms, an alkyl carbonate with the alkyl groups independently having 1 to 8 carbon atoms, an alkyl alcohol with the alkyl group having 1 to 8 carbon atoms, an aromatic hydrocarbon having 6 to 8 carbon atoms, an alkyl ketone with the alkyl groups independently having 1 to 8 carbon atoms, an alkyl glycol having 2 to 8 carbon atoms, a blend of (1) 1 to 75 weight % of an alkyl hydrocarbon having 5 to 10 carbon atoms and (2) 25 to 99 weight % of an alkyl ester having 2 to 8 carbon atoms, or water, or mixtures thereof.

25. The process of claim 22, wherein the solvent comprises methyl acetate, ethyl acetate, iso-butyl acetate, 2-ethylhexyl acetate, n-propyl propionate, n-butyl propionate, dimethyl carbonate, methanol, ethanol, n-butanol, 4-methyl-2-pentanol, 2-ethylhexanol, acetone, 4-methylpentan-2-one, 2,6-dimethylheptan-4-one, ethylene glycol, 1,4-cyclohexane dimethanol, benzene, toluene, xylene, a blend of primarily C8 hydrocarbons and an alkyl ester having 2 to 8 carbon atoms, a blend of (1) primarily C10 to C12 isoalkane hydrocarbons and (2) an alkyl ester having 2 to 8 carbon atoms, or water, or mixtures thereof.

26. The process of claim 23, wherein the solvent comprises an alkyl acetate with the alkyl group having 1 to 8 carbon atoms, an alkyl propionate with the alkyl group having 1 to 8 carbon atoms, an alkyl carbonate with the alkyl groups independently having 1 to 8 carbon atoms, an alkyl alcohol with the alkyl group having 1 to 8 carbon atoms, an aromatic hydrocarbon having 6 to 8 carbon atoms, an alkyl ketone with the alkyl groups independently having 1 to 8 carbon atoms, an alkyl glycol having 2 to 8 carbon atoms, a blend of (1) 1 to 75 weight % of an alkyl hydrocarbon having 5 to 10 carbon atoms and (2) 25 to 99 weight % of an alkyl ester having 2 to 8 carbon atoms, or water, or mixtures thereof.

27. The process of claim 23, wherein the solvent comprises methyl acetate, ethyl acetate, iso-butyl acetate, 2-ethylhexyl acetate, n-propyl propionate, n-butyl propionate, dimethyl carbonate, methanol, ethanol, n-butanol, 4-methyl-2-pentanol, 2-ethylhexanol, acetone, 4-methylpentan-2-one, 2,6-dimethylheptan-4-one, ethylene glycol, 1,4-cyclohexane dimethanol, benzene, toluene, xylene, a blend of (1) primarily C8 hydrocarbons and (2) an alkyl ester having 2 to 8 carbon atoms, a blend of (1) primarily C10 to C12 isoalkane hydrocarbons and (2) an alkyl ester having 2 to 8 carbon atoms, or water, or mixtures thereof.

28. A process for the crystallization of a mixture comprising cis-2,2,4,4-tetramethylcyclobutanediol and trans-2,2,4,4-tetramethylcyclobutanediol dissolved in a solvent, the process comprising:
   (a) crystallizing at least a portion of 2,2,4,4-tetramethylcyclobutanediol in a crystallization zone operated at a temperature such that the concentration of 2,2,4,4-tetramethylcyclobutanediol in the crystallization zone is above the saturated concentration of 2,2,4,4-tetramethylcyclobutanediol to form a slurry comprising crystallized 2,2,4,4-tetramethylcyclobutanediol and the solvent;
   (b) transferring the first slurry to a solid liquid separation zone wherein the first slurry is separated into a first mother liquor stream comprising the solvent and the dissolved 2,2,4,4-tetramethylcyclobutanediol and into a first wet cake stream comprising at least a portion of the crystallized 2,2,4,4-tetramethylcyclobutanediol;
   (c) transferring the first mother liquor stream to a second crystallization zone wherein 2,2,4,4-tetramethylcyclobutanediol is crystallized to form a second slurry comprising 2,2,4,4-tetramethylcyclobutanediol and the solvent;
   (d) transferring the second slurry to a second solid liquid separation zone,
   (e) separating the second slurry into a second mother liquor stream comprising the solvent and the dissolved 2,2,4,4-tetramethylcyclobutanediol and into a second wet cake stream comprising the crystallized 2,2,4,4-tetramethylcyclobutanediol;
   (f) transferring all of the second wet cake comprising solid cis-2,2,4,4-tetramethylcyclobutanediol and solid trans-2,2,4,4-tetramethylcyclobutanediol from the second solid liquid separation zone to the first crystallization zone,
wherein the solvent comprises an alkyl acetate, an alkyl propionate, an alkyl carbonate, an alkyl alcohol, an aromatic hydrocarbon, an alkyl ketone, an alkyl glycol, a blend of (1) an alkyl hydrocarbon and (2) an alkyl ester, or water or mixtures thereof.

29. The process of claim 28, wherein the solvent comprises an alkyl acetate with the alkyl group having 1 to 8 carbon atoms, an alkyl propionate with the alkyl group having 1 to 8 carbon atoms, an alkyl carbonate with the alkyl groups independently having 1 to 8 carbon atoms, an alkyl alcohol with the alkyl group having 1 to 8 carbon atoms, an aromatic hydrocarbon having 6 to 8 carbon atoms, an alkyl ketone with the alkyl groups independently having 1 to 8 carbon atoms, an alkyl glycol having 2 to 8 carbon atoms, a blend of (1) 1 to 75 weight % of an alkyl hydrocarbon having 5 to 10 carbon atoms and (2) 25 to 99 weight % of an alkyl ester with 2 to 8 carbon atoms, or water, or mixtures thereof.

30. The process of claim 28, wherein the solvent comprises methyl acetate, ethyl acetate, iso-butyl acetate, 2-ethylhexyl acetate, n-propyl propionate, n-butyl propionate, dimethyl carbonate, methanol, ethanol, n-butanol, 4-methyl-2-pentanol, 2-ethylhexanol, acetone, 4-methylpentan-2-one, 2,6-dimethylheptan-4-one, ethylene glycol, 1,4-cyclohexane dimethanol, benzene, toluene, xylene, a blend of primarily C8 hydrocarbons and an alkyl ester having 2 to 8 carbon atoms, a blend of (1) primarily C10 to C12 isoalkane hydrocarbons and (2) an alkyl ester with 2 to 8 carbon atoms, or water, or mixtures thereof.

* * * * *